(12) United States Patent
Bellisario et al.

(10) Patent No.: US 8,187,231 B2
(45) Date of Patent: May 29, 2012

(54) CATHETERIZATION SYSTEM

(75) Inventors: Marc Bellisario, Tewksbury, MA (US);
Mark Lotito, Wrentham, MA (US);
Kurt E. Green, Wrentham, MA (US);
Geoffrey McElroy, Auburn, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 2 days.

(21) Appl. No.: 12/821,640

(22) Filed: Jun. 23, 2010

(65) Prior Publication Data
US 2010/0331780 A1    Dec. 30, 2010

Related U.S. Application Data

(63) Continuation of application No. 61/220,656, filed on Jun. 26, 2009.

(51) Int. Cl.
*A61M 5/178* (2006.01)
*A61M 5/32* (2006.01)
*A61M 3/00* (2006.01)

(52) U.S. Cl. ......... 604/164.06; 604/164.01; 604/165.01; 604/272; 604/43

(58) Field of Classification Search ................. 604/6.16, 604/43, 44, 6.06, 4.01, 5.01, 27, 164.01, 604/164.05–164.09, 164.13, 165.01, 165.02, 604/171, 272, 273, 523, 524
See application file for complete search history.

(56) References Cited

U.S. PATENT DOCUMENTS

| | | | |
|---|---|---|---|
| 701,075 A | 5/1902 | McCully |
| 2,541,691 A | 2/1951 | Eicher |
| D208,838 S | 10/1967 | St. Amand |
| 4,134,402 A | 1/1979 | Mahurkar |
| D254,270 S | 2/1980 | Ziegler |
| 4,306,562 A | 12/1981 | Osborne |
| D272,651 S | 2/1984 | Mahurkar |
| 4,443,333 A | 4/1984 | Mahurkar |

(Continued)

FOREIGN PATENT DOCUMENTS

CA    2389227    10/2001

(Continued)

OTHER PUBLICATIONS

International Search Report dated Aug. 23, 2010 for copending International Appln. No. PCT/US2010/039633.

*Primary Examiner* — Jackie Ho
*Assistant Examiner* — Leah Stohr
(74) *Attorney, Agent, or Firm* — Thomas M. Johnston, Esq.

(57) ABSTRACT

The present disclosure relates to catheterization systems and components thereof. In one embodiment of the present disclosure, a catheterization system is disclosed that includes a catheter including a body with proximal and distal ends and defining first and second lumens extending therethrough, and a stylet. The stylet includes first and second stylet portions each having proximal and distal end regions, wherein the distal end regions of the first and second stylet portions together define a tapered penetrating portion. The first and second stylet portions are configured and dimensioned to be slidably positioned within the first and second lumens of the catheter, respectively. The first and second stylet portions extend from the proximal end of the catheter and beyond the distal end of the catheter, and are independently movable in relation to each other to facilitate selective removal of the first stylet portion and/or the second stylet portion from the catheter.

21 Claims, 19 Drawing Sheets

U.S. PATENT DOCUMENTS

| | | |
|---|---|---|
| 4,568,329 A | 2/1986 | Mahurkar |
| 4,583,968 A | 4/1986 | Mahurkar |
| 4,601,697 A | 7/1986 | Mammolenti et al. |
| 4,604,379 A | 8/1986 | Twardowski et al. |
| D289,682 S | 5/1987 | Dragan |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Mahurkar |
| D292,825 S | 11/1987 | Dragan |
| 4,770,652 A | 9/1988 | Mahurkar |
| 4,772,269 A | 9/1988 | Twardowski et al. |
| D298,461 S | 11/1988 | Manno |
| 4,798,193 A | 1/1989 | Giesy et al. |
| 4,808,155 A | 2/1989 | Mahurkar |
| 4,824,435 A | 4/1989 | Giesy et al. |
| 4,842,582 A | 6/1989 | Mahurkar |
| 4,883,426 A | 11/1989 | Ferrer |
| 4,894,057 A | 1/1990 | Howes |
| 4,895,561 A | 1/1990 | Mahurkar |
| 4,904,238 A | 2/1990 | Williams |
| D312,872 S | 12/1990 | Mahl |
| 4,988,356 A | 1/1991 | Crittenden et al. |
| 5,009,636 A | 4/1991 | Wortley et al. |
| 5,015,184 A | 5/1991 | Perry et al. |
| 5,167,623 A | 12/1992 | Cianci et al. |
| 5,171,227 A | 12/1992 | Twardowski et al. |
| 5,197,951 A | 3/1993 | Mahurkar |
| 5,209,723 A | 5/1993 | Twardowski et al. |
| 5,221,255 A | 6/1993 | Mahurkar |
| 5,221,256 A | 6/1993 | Mahurkar |
| 5,273,527 A | 12/1993 | Schatz et al. |
| 5,281,134 A | 1/1994 | Schultz |
| 5,282,788 A | 2/1994 | Wilk et al. |
| 5,290,282 A | 3/1994 | Casscells |
| 5,318,518 A | 6/1994 | Plechinger et al. |
| 5,318,527 A | 6/1994 | Hyde et al. |
| 5,320,605 A | 6/1994 | Sahota |
| 5,336,165 A | 8/1994 | Twardowski |
| 5,336,184 A | 8/1994 | Teirstein |
| 5,374,245 A | 12/1994 | Mahurkar |
| 5,378,230 A | 1/1995 | Mahurkar |
| 5,395,332 A | 3/1995 | Ressemann et al. |
| 5,403,291 A | 4/1995 | Abrahamson |
| 5,405,320 A | 4/1995 | Twardowski |
| 5,405,341 A | 4/1995 | Martin |
| 5,419,777 A | 5/1995 | Hofling |
| 5,443,457 A | 8/1995 | Ginn et al. |
| 5,451,216 A | 9/1995 | Quinn |
| 5,458,584 A | 10/1995 | Ginn et al. |
| 5,464,398 A | 11/1995 | Haindl |
| 5,484,397 A | 1/1996 | Twardowski |
| 5,486,159 A | 1/1996 | Mahurkar |
| 5,509,897 A | 4/1996 | Twardowski et al. |
| 5,536,234 A | 7/1996 | Newman |
| 5,549,541 A | 8/1996 | Muller |
| 5,554,136 A | 9/1996 | Luther |
| 5,562,640 A | 10/1996 | McCabe et al. |
| 5,569,182 A | 10/1996 | Twardowski et al. |
| 5,571,087 A | 11/1996 | Ressemann et al. |
| 5,571,093 A | 11/1996 | Cruz et al. |
| 5,607,440 A | 3/1997 | Danks et al. |
| 5,685,867 A | 11/1997 | Twardowski et al. |
| 5,707,351 A | 1/1998 | Dorsey, III |
| 5,725,495 A | 3/1998 | Strukel et al. |
| 5,776,092 A | 7/1998 | Farin et al. |
| 5,782,797 A | 7/1998 | Schweich, Jr. et al. |
| 5,785,678 A | 7/1998 | Griep et al. |
| 5,788,680 A | 8/1998 | Linder |
| 5,788,681 A | 8/1998 | Weaver et al. |
| 5,801,012 A | 9/1998 | Soff et al. |
| 5,830,196 A | 11/1998 | Hicks |
| 5,858,009 A | 1/1999 | Jonkman |
| 5,902,476 A | 5/1999 | Twardowski |
| 5,961,486 A | 10/1999 | Twardowski et al. |
| 6,059,748 A | 5/2000 | Teirstein et al. |
| 6,063,099 A | 5/2000 | Danks et al. |
| 6,086,565 A | 7/2000 | Ouchi |
| 6,126,631 A | 10/2000 | Loggie |
| 6,129,738 A | 10/2000 | Lashinski et al. |
| 6,132,456 A | 10/2000 | Sommer et al. |
| 6,132,616 A | 10/2000 | Twardowski et al. |
| 6,146,536 A | 11/2000 | Twardowski |
| 6,152,910 A | 11/2000 | Agro et al. |
| 6,190,357 B1 | 2/2001 | Ferrari et al. |
| 6,299,444 B1 | 10/2001 | Cohen |
| 6,409,700 B1 | 6/2002 | Siegel, Jr. et al. |
| 6,423,050 B1 | 7/2002 | Twardowski |
| 6,428,502 B1 | 8/2002 | Lang |
| 6,576,609 B1 | 6/2003 | Soff et al. |
| 6,592,565 B2 | 7/2003 | Twardowski |
| 6,916,313 B2 | 7/2005 | Cunningham |
| 7,141,035 B2 | 11/2006 | Haggstrom |
| 2002/0065492 A1 | 5/2002 | McGuckin, Jr. et al. |
| 2003/0013985 A1 | 1/2003 | Saadat |
| 2003/0212373 A1* | 11/2003 | Hall et al. ............... 604/263 |
| 2004/0087892 A1* | 5/2004 | Cunningham ............ 604/43 |
| 2004/0193046 A1 | 9/2004 | Nash et al. |
| 2004/0243095 A1* | 12/2004 | Nimkar et al. ............ 604/500 |
| 2005/0096585 A1* | 5/2005 | Schon et al. ............. 604/43 |
| 2005/0131449 A1 | 6/2005 | Salahieh et al. |
| 2006/0116629 A1* | 6/2006 | Tal et al. ................. 604/43 |
| 2009/0112167 A1* | 4/2009 | Haarala et al. ......... 604/167.03 |

FOREIGN PATENT DOCUMENTS

| | | |
|---|---|---|
| EP | 0107810 | 5/1984 |
| EP | 0341721 | 11/1989 |
| EP | 0555780 | 8/1993 |
| EP | 0623356 | 11/1994 |
| FR | 2326941 | 10/1976 |
| GB | 2028136 | 3/1980 |
| JP | 08103492 | 4/1996 |
| JP | 8-308933 | 11/1996 |
| WO | WO 92/14500 | 9/1992 |
| WO | WO 95/10317 | 4/1995 |
| WO | WO 99/38550 | 8/1999 |

* cited by examiner

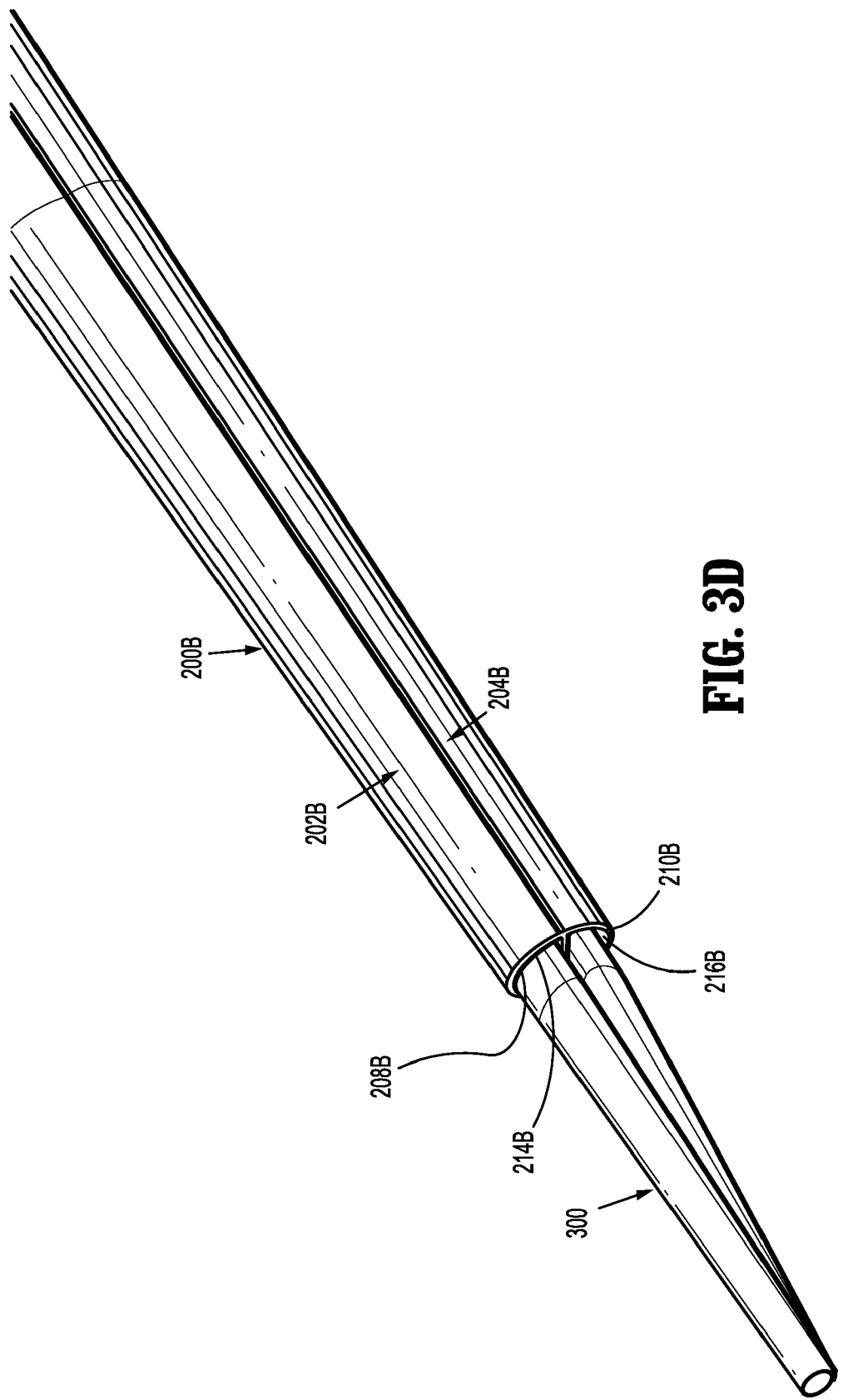

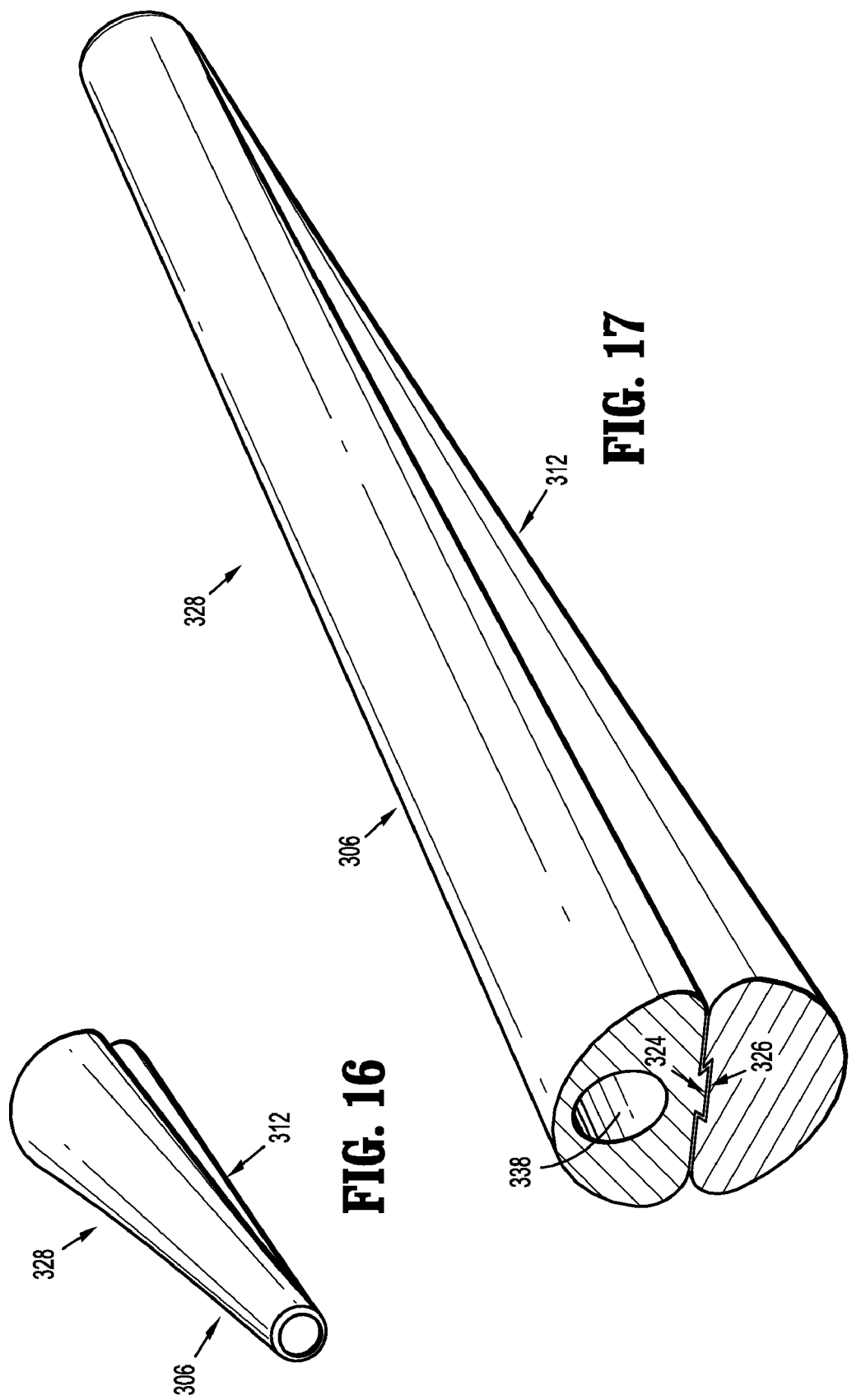

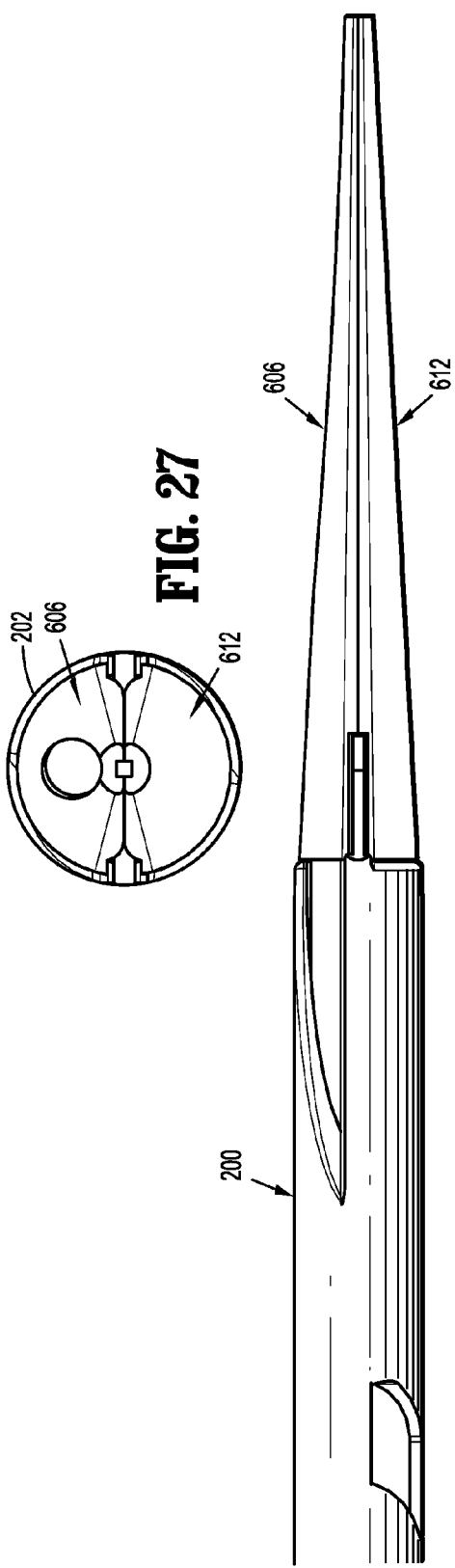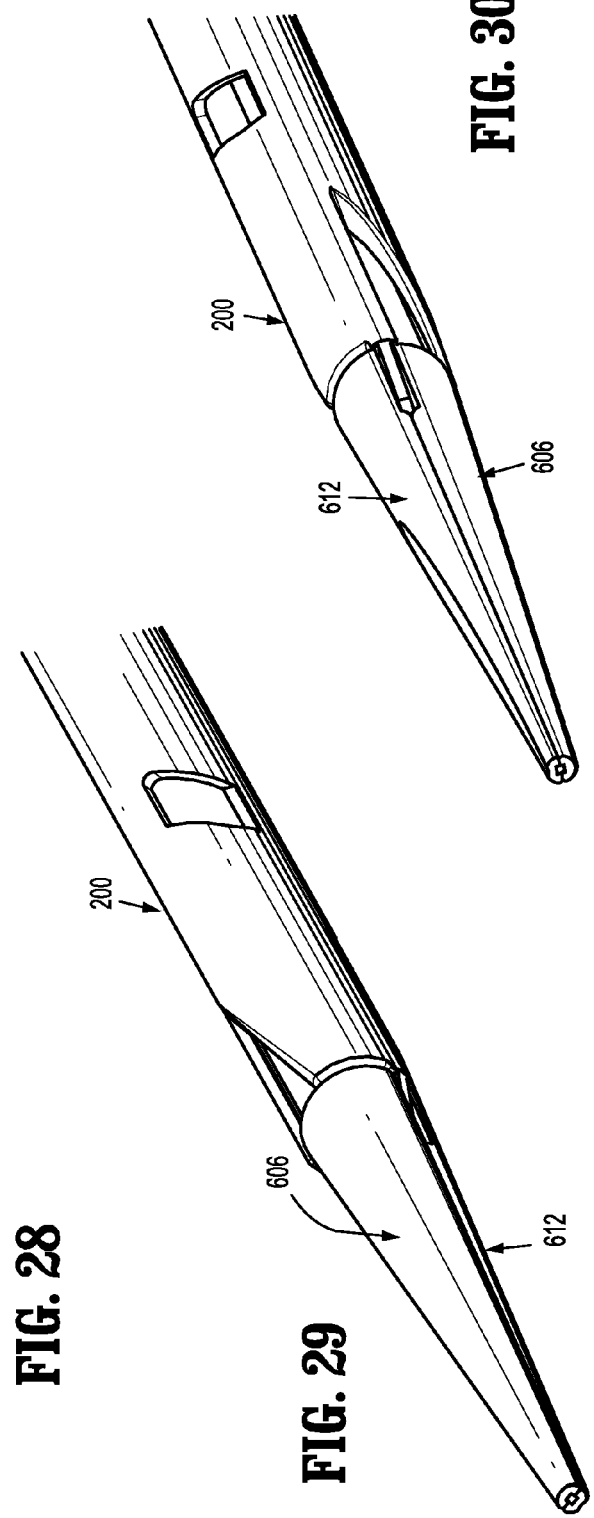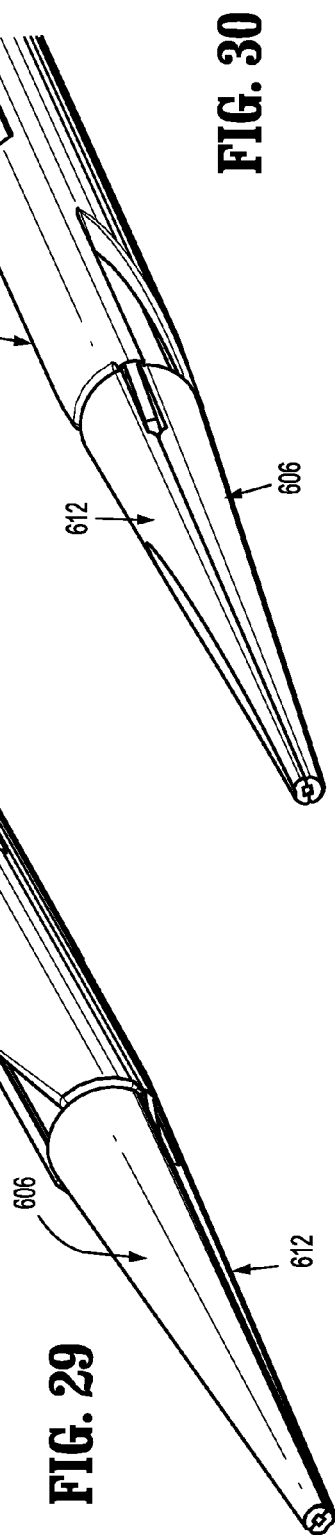

CATHETERIZATION SYSTEM

CROSS-REFERENCE TO RELATED APPLICATIONS

The present application claims the benefit of U.S. Provisional Patent Application Ser. No. 61/220,656, filed on Jun. 26, 2009, the entire contents of which are incorporated by reference herein.

BACKGROUND

1. Technical Field

The present disclosure is directed to a catheter assembly adapted for use in a catheterization procedure. Specifically, the present disclosure relates to insertion sheaths and stylets for use during implantation of a catheter assembly during a hemodialysis procedure.

2. Description of the Related Art

Catheters are flexible medical instruments for use in the withdrawal and introduction of fluids to and from body cavities, ducts, and vessels. Catheters have particular application in hemodialysis procedures, in which blood is withdrawn from a blood vessel for treatment and subsequently returned to the blood vessel for circulation through a patient's body.

Many hemodialysis catheters include multiple lumens, e.g., dual or triple-lumen catheters, with one lumen being dedicated to the withdrawal of fluid from a vessel, and at least one other lumen being dedicated to the return of fluid to the vessel. Generally, the lumen through which fluid is withdrawn is referred to as the "arterial" lumen, and the lumen through which fluid is returned is referred to as the "venous" lumen. During an exemplary hemodialysis procedure, after placement of a multiple lumen catheter in a patient, blood is withdrawn from the patient through the arterial lumen of the catheter, and is directed to a hemodialysis unit for dialysis, i.e., to remove waste and toxins from the blood. The dialyzed blood is then returned to the patient through the venous lumen of the catheter.

Various techniques are employed for the insertion of hemodialysis catheters including, e.g., the use of guidewires, introduction stylets, and the like. During such procedures, the stylet is inserted through the catheter and is used to facilitate introduction of the catheter en route to a target site. After placement of the catheter, the stylet is removed, and a proximal end of the catheter is fluidly connected to a catheter hub, with or without extension tubes. One insertion technique is disclosed in U.S. Pat. No. 5,509,897 to Twardowski et al., the contents of which are incorporated herein in their entirety.

Generally, hemodialysis catheters are categorized as either acute or chronic in nature. Acute catheters are designed to be placed in a patient under emergent circumstances where delays in placement are unacceptable, and typically remain in place for only a few days. Chronic catheters, by contrast, typically remain in place for extended periods of time, and may be implanted via surgical dissection, e.g., at the patient's bedside, or in an ambulatory surgical setting.

In general, more rigid catheters are easier to insert when compared to more flexible catheters due to kinking and buckling that results during advancement of the catheter through the patient's tissue. As such, acute catheters are often more rigid than chronic catheters given the urgency of placement. While more flexible catheters may have a reduced risk of patient trauma, and may result in increased patient comfort, these catheters normally require the use of an insertion device to assist in placement, e.g., an insertion sheath or stylet.

It would thus be advantageous to provide structure employable in the placement of flexible catheters to achieve the benefits of insertion associated with rigid catheters without compromise regarding reduced patient trauma and increased patient comfort.

SUMMARY

In one embodiment of the present disclosure, a catheterization system is disclosed including a catheter with a body having proximal and distal ends and defining first and second lumens extending therethrough, and a stylet. The catheter is formed from a first material, and the stylet is formed from a second, more rigid material such that positioning of the stylet within the catheter increases rigidity of the catheter.

The stylet includes a first stylet portion having proximal and distal end regions, and a second stylet portion having proximal and distal end regions. The first stylet portion is configured and dimensioned to be slidably positioned within the first lumen of the catheter, and the second stylet portion is configured and dimensioned to be slidably positioned within the second lumen of the catheter. The first and second stylet portions extend from the proximal end of the catheter and beyond the distal end of the catheter, and are independently movable in relation to each other to facilitate selective removal of the first stylet portion and/or the second stylet portion from the catheter. The distal end regions of the first and second stylet portions are substantially coterminous, and together define a tapered penetrating portion.

In one embodiment of the present disclosure, the first and second stylet portions include corresponding mating structure positioned at the distal end regions thereof. The corresponding mating structure is configured to facilitate relative slidable movement between the first and second stylet portions. For example, the mating structure included on the first stylet portion may include a rib, and the mating structure included on the second stylet portion may include a channel that is configured and dimensioned to slidably receive the rib. It is envisioned that the rib and the channel may be configured and dimensioned to allow relative transverse movement between the first and second stylet portions, or that the rib and the channel may be configured and dimensioned to prevent such relative transverse movement, e.g., the rib and the channel may each include a dovetail configuration.

The first stylet portion corresponds in configuration to the first lumen of the catheter, and may define a channel therethrough that is configured and dimensioned to receive a guidewire. Similarly, the second stylet portion corresponds in configuration to the second lumen of the catheter.

In one embodiment, the catheterization system may further include a sheath having proximal and distal ends and defining a sheath lumen configured and dimensioned to receive the catheter. In this embodiment of the disclosed catheterization system, the stylet is dimensioned to extend beyond the distal end of the sheath when the stylet is positioned within the catheter such that the sheath forces the distal end regions of the first and second stylet portions into engagement with each other to define the penetrating portion of the stylet. To facilitate tearing of the sheath, the sheath may include a perforated section.

In another aspect of the present disclosure, an insertion stylet is disclosed for use with a catheter including a body defining first and second lumens extending therethrough. The disclosed insertion stylet includes a first stylet portion that is configured and dimensioned for positioning within the first lumen of the catheter, and a second stylet portion that is configured and dimensioned for positioning within the second lumen of the catheter. The first and second stylet portions are configured and dimensioned for independent, selective insertion into, and removal from, the catheter. Together, the first and second stylet portions define a tapered penetration portion.

It is envisioned that the first and second stylet portions may include distal end regions incorporating corresponding mating structure that is configured and dimensioned to facilitate relative slidable movement of the first and second stylet portions. For example, the mating structure included on the first stylet portion may include a rib, and the mating structure included on the second stylet portion may include a channel configured and dimensioned to slidably receive the rib.

In yet another aspect of the present disclosure, a method of positioning a catheter within a tissue site is disclosed that includes the steps of (i) positioning a first stylet portion of a stylet within a first lumen of the catheter and positioning a second stylet portion of the stylet within a second lumen of the catheter, wherein the first and second stylet portions extend from a proximal end of the catheter and beyond a distal end of the catheter; (ii) positioning the stylet and the catheter within an introducer sheath to thereby form a catheter assembly; (iii) advancing the catheter assembly distally over a guidewire positioned within the tissue site until a distal end of the catheter is positioned within the tissue site; (iv) withdrawing the stylet from the catheter; and (v) splitting the sheath to thereby reveal the catheter.

The step of withdrawing the stylet from the catheter may include sequentially withdrawing the first stylet portion and the second stylet portion. Additionally, or alternatively, the disclosed method may further include the step of attaching corresponding mating structure provided at distal end regions of the first and second stylet portions to thereby connect a distal end region of the first stylet portion to a distal end region of the second stylet portion such that the first and second stylet portions are independently movable.

In still another aspect of the present disclosure, a catheterization system is disclosed that includes a catheter and a stylet.

The catheter includes a body with proximal and distal ends, and defines first and second lumens extending therethrough that are separated by a septum wall.

The stylet includes a first stylet portion with proximal and distal end regions, wherein the first stylet portion is configured and dimensioned for insertion into the first lumen of the catheter, and a second stylet portion with proximal and distal end regions, wherein the second stylet portion is configured and dimensioned for insertion into the second lumen of the catheter. Whereas the proximal end regions of the first and second stylet portions are separated from one another, the distal end regions of the first and second stylet portions are conjoined, to thereby inhibit relative longitudinal movement between the first and second stylet portions until a predetermined force is applied to the stylet.

The distal end regions of the first and second stylet portions are connected by conjoining structure, such as, for example, a weld. The conjoining structure is configured, dimensioned, and positioned such that the predetermined force is applied to the conjoining structure by the septum wall of the catheter upon withdrawal of at least one of the first and second stylet portions from the catheter, whereby the first stylet portion is separated from the second stylet portion to permit relative longitudinal movement therebetween.

In another aspect of the present disclosure, a method of positioning a catheter within a tissue site is disclosed that includes the steps of (i) positioning first and second stylet portions of a stylet within corresponding lumens of the catheter such that distal end regions of the first and second stylet portions extend beyond a distal end of the catheter; (ii) joining together distal end regions of the first and second stylet portions in a manner inhibiting relative longitudinal movement between the first and second stylet portions; (iii) advancing the stylet and the catheter distally over a guidewire positioned within the tissue site until a distal end of the catheter is positioned within the tissue site; (iv) applying a proximally directed force to at least one of the first and second stylet portions to thereby separate the distal end regions of the first and second stylet portions, and permit relative longitudinal movement between the first and second stylet portions; and (v) withdrawing the stylet from the catheter.

In a final aspect of the present disclosure, a method of positioning a catheter within a tissue site is disclosed that includes the steps of (i) positioning first and second stylet portions of a stylet within corresponding lumens of the catheter separated by a septum wall such that distal end regions of the first and second stylet portions extend beyond a distal end of the catheter; (ii) joining together distal end regions of the first and second stylet portions at conjoining structure in a manner inhibiting relative longitudinal movement between the first and second stylet portions; (iii) advancing the stylet and the catheter distally over a guidewire positioned within the tissue site until a distal end of the catheter is positioned within the tissue site; (iv) applying a proximally directed force to at least one of the first and second stylet portions to thereby cause engagement of the conjoining structure with the septum wall, and separation of the distal end regions of the first and second stylet portions, to facilitate relative longitudinal movement between the first and second stylet portions; and (iv) withdrawing the stylet from the catheter.

BRIEF DESCRIPTION OF THE DRAWINGS

Various embodiments of the present disclosure will be described herein with references to the accompanying drawings, wherein:

FIG. 3D is an isometric view of the catheter and the insertion stylet seen in FIG. 3C;

FIG. 16 is a partial front, perspective view of the distal end regions of the first and second stylet portions upon engagement;

FIG. 17 is a partial, rear, cross-sectional view of the distal end regions of the first and second stylet portions upon engagement shown in perspective;

FIG. 27 is a partial front view of the distal end regions of the first and second stylet portions shown in FIG. 22 upon engagement and positioned within the catheter seen in FIG. 2;

FIG. 28 is a partial side view of the distal end regions of the first and second stylet portions shown in FIG. 22 upon engagement and positioned within the catheter seen in FIG. 2;

FIGS. 29 and 30 are partial side, perspective views of the distal end regions of the first and second stylet portions shown in FIG. 22 upon engagement and positioned within the catheter seen in FIG. 2;

DETAILED DESCRIPTION OF THE EMBODIMENTS

Various exemplary embodiments of the present disclosure are discussed herein below in terms of medical catheters for the administration of fluids, i.e., withdrawal and introduction, to and from the body of a patient and, more particularly, in terms of a hemodialysis catheter. However, it is envisioned that the principles of the present disclosure are equally applicable to a range of catheter applications including surgical, diagnostic and related treatments of diseases and body ailments of a subject. It is further envisioned that the principles relating to the presently disclosed catheter may be equally applicable to a variety of catheter related procedures, such as, for example, hemodialysis, cardiac, abdominal, urinary, and intestinal procedures, in chronic and acute applications. Moreover, the presently disclosed catheter can be used for administration and removal of fluids such as, for example, medication, saline, bodily fluids, blood and urine.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human patient or other animal, and the term "clinician" should be understood as referring to a doctor, nurse or other care provider and may include support personnel.

The following discussion includes a description of the presently disclosed catheterization system and corresponding stylet, followed by a description of an exemplary corresponding method of use in accordance with the principles of the present disclosure. For the purposes of discussion, the catheterization system, stylet, and other components will be discussed in terms of a hemodialysis catheter, and the corresponding method of use will be discussed in terms of a tunneling procedure utilized for positioning a catheter during a dialysis procedure. However, those skilled in the art will appreciate the presently disclosed catheterization system, and the components thereof, have many other applications in addition to dialysis applications.

Figure 1:
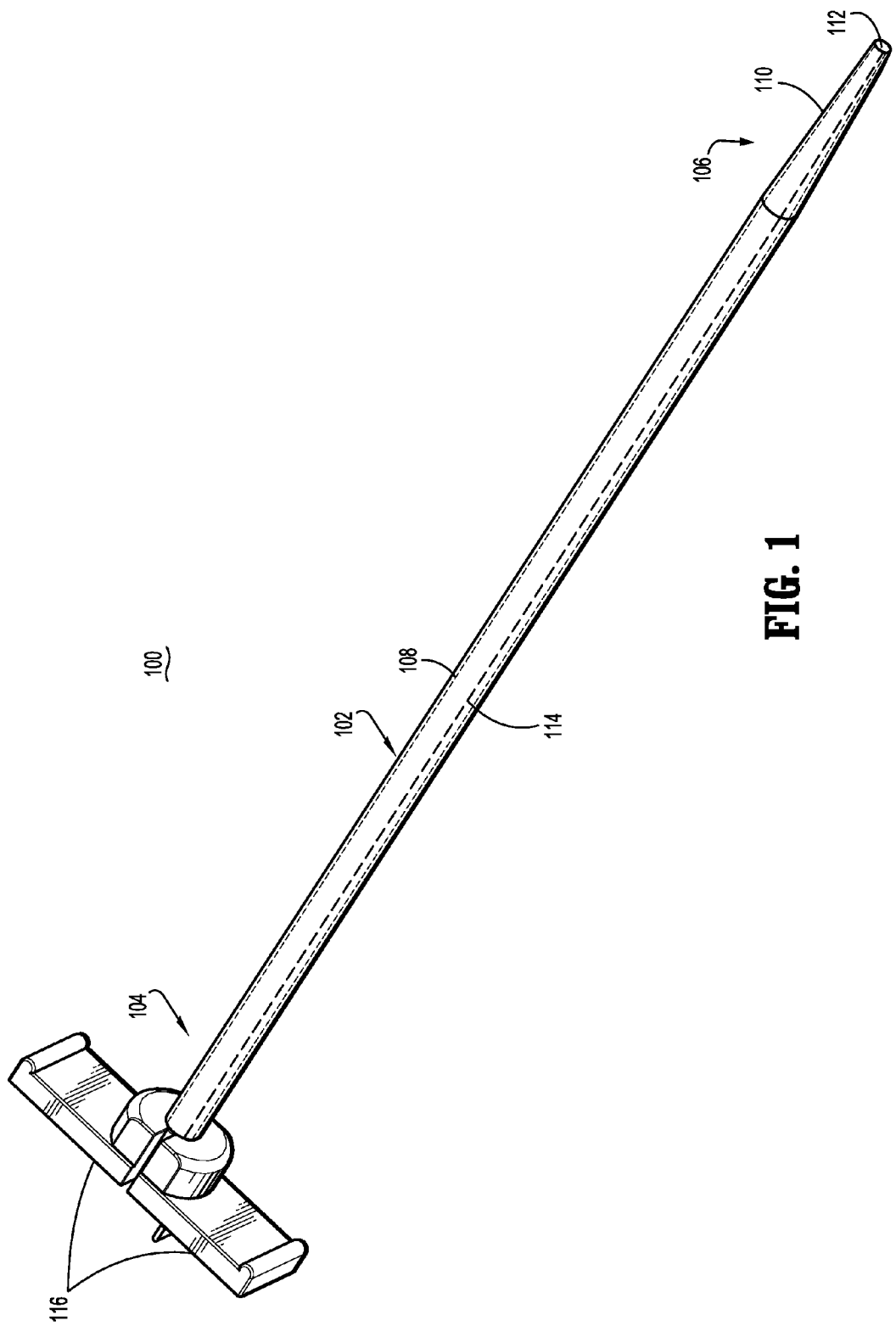
FIG. 1 is a side, perspective view of an introducer sheath in accordance with one aspect of the present disclosure.
Figure 2:
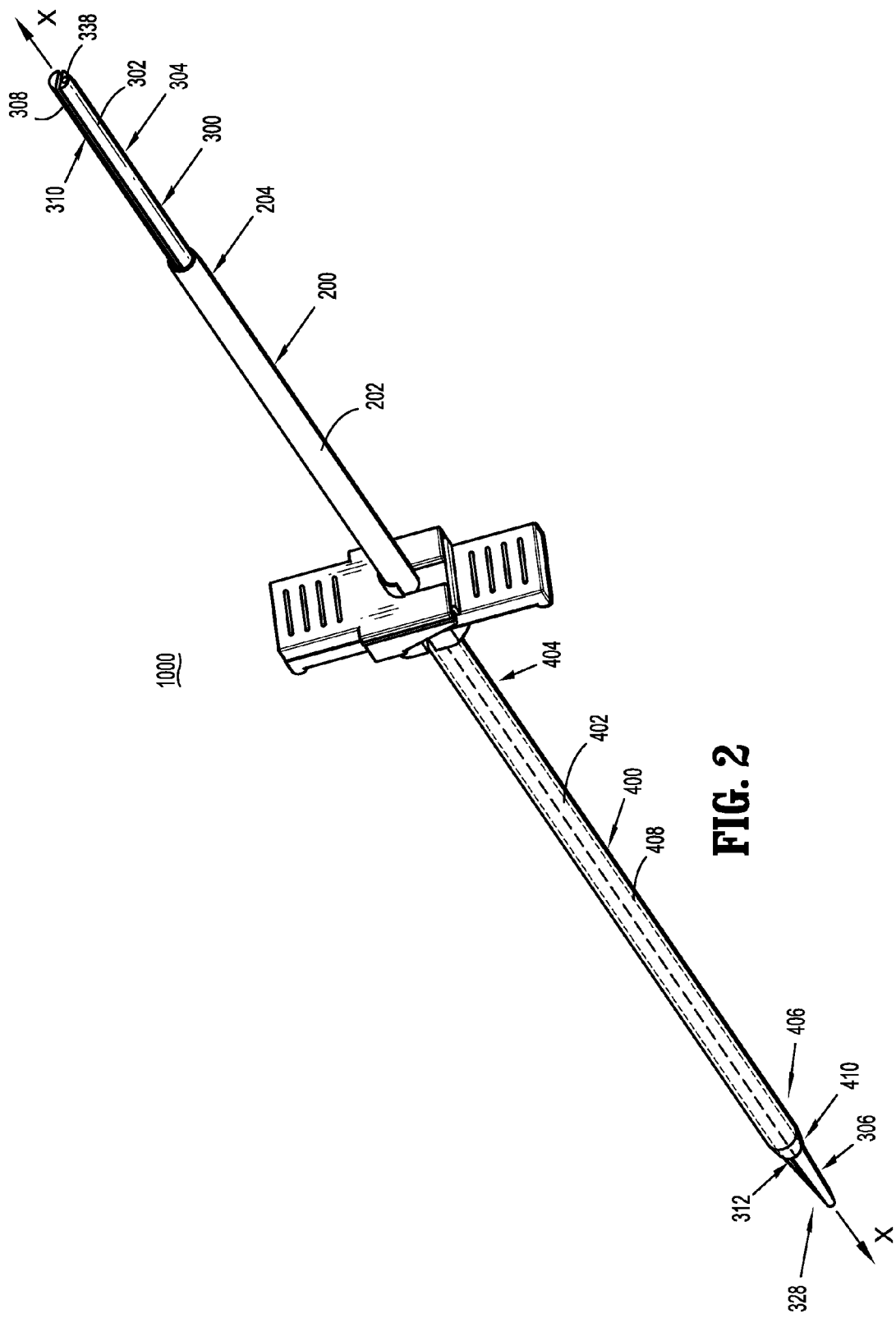
FIG. 2 is a front, perspective view of a catheterization system including an insertion stylet with first and second stylet portions, a catheter, and an introducer sheath in accordance another aspect of the present disclosure.

Referring now to the figures, wherein like components are designated by like reference numerals throughout the several views, FIG. 1 illustrates one embodiment of an introducer sheath, referred to generally by the reference character 100, for use in the placement of a catheter in a patient, such as the catheter 200 seen in FIG. 2. The introducer sheath 100 includes a tubular body portion 102 having a proximal region 104 and a distal region 106. The body portion 102 of the introducer sheath 100 defines an internal lumen 108 (shown in phantom in FIG. 1) that is configured and dimensioned to slidably receive the catheter 200 (FIG. 2).

The distal region 106 of the introducer sheath 100 includes a distally tapered penetrating portion 110 that is configured and dimensioned to enlarge an opening formed in target tissue, e.g., a blood vessel, during distal advancement of the introducer sheath 100. The penetrating portion 110 is fixedly secured to, e.g., monolithically formed with, the body portion 102, and includes a distal opening 112 that is configured and dimensioned to receive a guidewire (not shown). In one embodiment of the introducer sheath 100, it is contemplated that the distal opening 112 may define an internal transverse dimension that substantially approximates an outer dimension of the guidewire to minimize surface area at the distal-most end of the penetration portion 110, and thereby minimize trauma to the patient's tissue during introduction of the introducer sheath 100 into a patient.

In the embodiment of the introducer sheath 100 illustrated in FIG. 1, the introducer sheath 100 includes one or more perforations 114, e.g., diametrically opposed perforations, to facilitate tearing or splitting of the introducer sheath 100. Specifically, following placement of the catheter 200 (FIG. 2) in the target tissue as desired, the clinician can tear, or split, the introducer sheath 100 along the perforation(s) 114 to facilitate separation of the introducer sheath 100 from the catheter 200 (FIG. 2). To facilitate such tearing, the introducer sheath 100 may include manual grips or members 116 positioned in the proximal region 104 of the introducer sheath 100 that are configured and dimensioned for engagement by the clinician.

Although not illustrated, it is envisioned that the introducer sheath 100 may include one or more valve members positioned within the internal lumen 108 that are configured and dimensioned to inhibit fluid communication through the introducer sheath 100. For example, the valve member(s) may be configured and dimensioned to inhibit blood loss and/or air emboli. However, it is also envisioned that the distal opening 112 may be sized to closely fit the guidewire such that a valve member may not be necessary.

Referring now to FIG. 2, a catheterization system 1000 in accordance with the present disclosure will be discussed. The catheterization system 1000 includes the catheter 200 mentioned above during the discussion of FIG. 1, an insertion stylet 300 that is configured and dimensioned for removable positioning within the catheter 200, and an introducer sheath 400 that is configured and dimensioned to removably receive the catheter 200.

FIG. 2 illustrates the catheter 200 positioned within the introducer sheath 400, and the stylet 300 positioned within the catheter 200. Throughout the following discussion, the catheter 200 will be discussed, and illustrated in the corresponding figures, as a dual lumen catheter including a Spiral-Z tip configuration (FIGS. 2A-2D), which has particular application in a hemodialysis procedure. It should be appreciated, however, that the principles of the present disclosure are equally applicable to catheters having alternative tip configurations, such as staggered tip catheters (FIGS. 3A, 3B) or split-tip catheters (FIGS. 3C, 3D), catheters including additional lumens, such as triple lumen catheters, and/or catheters that are employable in a variety of other medical procedures.

Figure 2A:
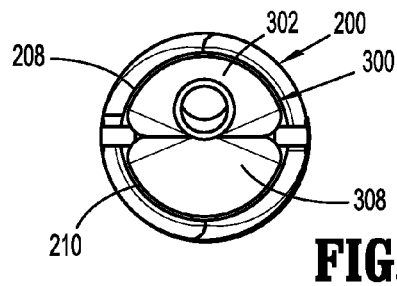
FIG. 2A is a front view illustrating the first and second stylet portions seen in FIG. 2 positioned within the catheter.
Figure 2B:
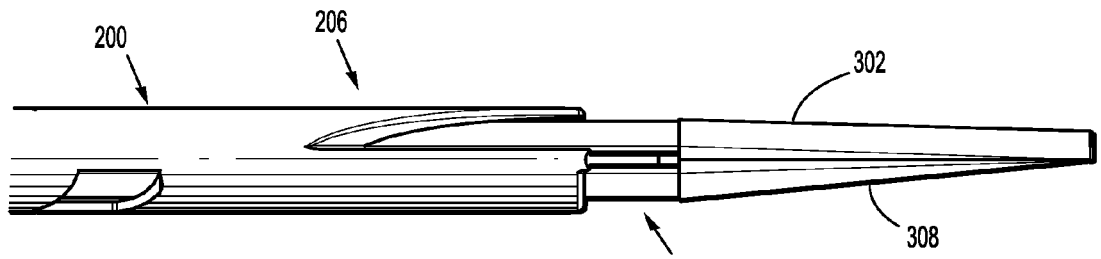
FIG. 2B is a partial side view of the first and second stylet portions positioned within the catheter and extending beyond a distal end thereof.
Figure 2C:
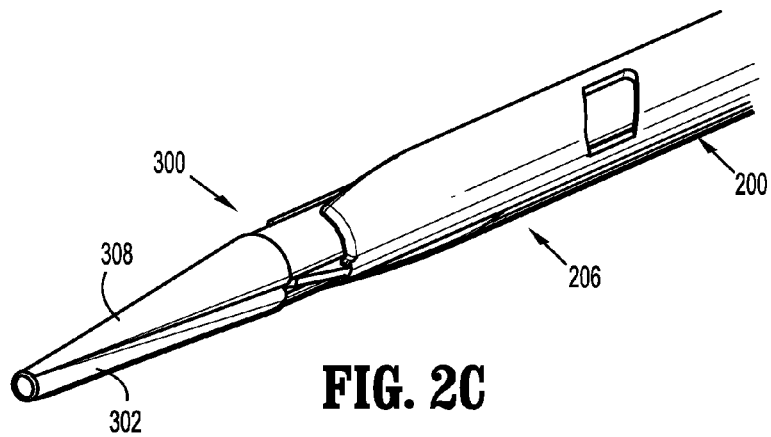
FIGS. 2C and 2D are partial side, perspective views of the first and second stylet portions positioned within the catheter and extending beyond a distal end thereof.
Figure 2D:
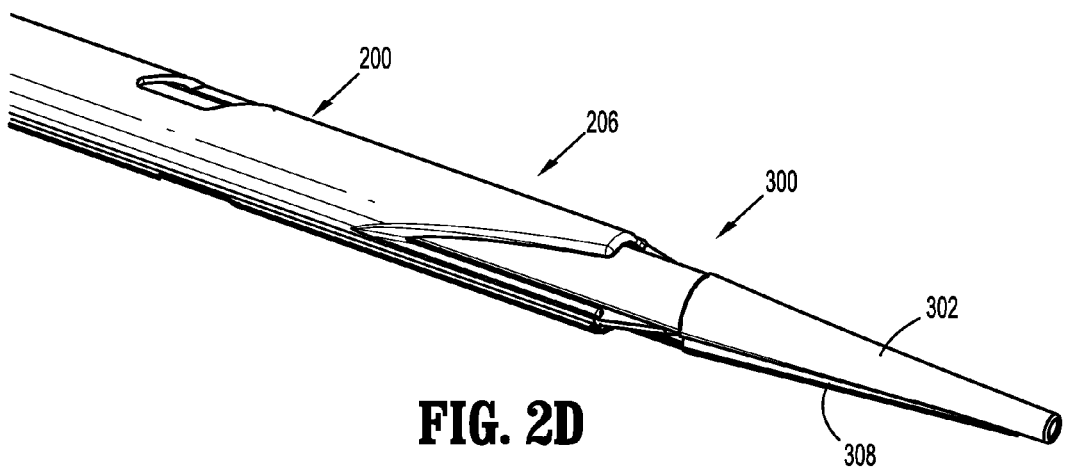
Figure 3:
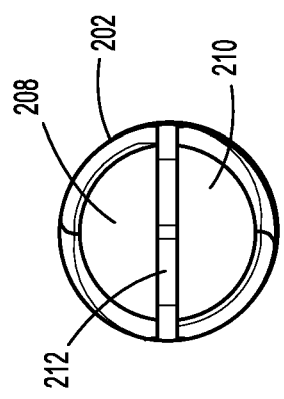
FIG. 3 is a front view of the catheter seen in FIG. 2, with the first and second stylet portions removed, illustrating a dual lumen configuration.

Referring now to FIGS. 2-3, the catheter 200 includes a body 202 with respective proximal and distal ends 204, 206, and first and second lumens 208, 210 (FIGS. 2A, 3) extending therebetween that are separated by a septum wall 212. While each of the respective first and second lumens 208, 210 extending through the catheter 200 are illustrated as including substantially D-shaped cross-sectional configurations, it should be appreciated that other configurations for the lumens 208, 210 are also contemplated herein, including but not limited to substantially circular or pie shaped lumens.

The catheter 200 is formed form a flexible material, and may be formed through any suitable method of manufacture, including but not limited to, conventional injection molding and extrusion processes. If necessary or desired, to increase stability and rigidity, the catheter 200 may include a reinforcing material. The catheter 200 may include a pre-curved configuration in a normal state thereof, wherein the catheter assumes an arcuate profile in the absence of any external forces, such that the catheter 200 may conform to the configuration of the target tissue, e.g., the body cavity or vessel in which the catheter 200 is to be positioned. Alternatively, the catheter 200 may be devoid of any such normally curved configuration.

Suitable non-exclusive examples of catheters 200 falling within the scope of the present disclosure are the Tal PALINDROME™ and MAHURKAR® Maxid™ catheters, each of which is made available by Covidien, which maintains a principal place of business at 15 Hampshire Street, Mansfield, Mass. Other examples of suitable catheters are disclosed in U.S. patent application Ser. No. 11/528,913, filed Sep. 25, 2006, and U.S. Pat. No. 7,182,746 to Haarala, et al., filed Feb. 11, 2005, the entire contents of each of these references being incorporated by reference herein.

Figure 3A:
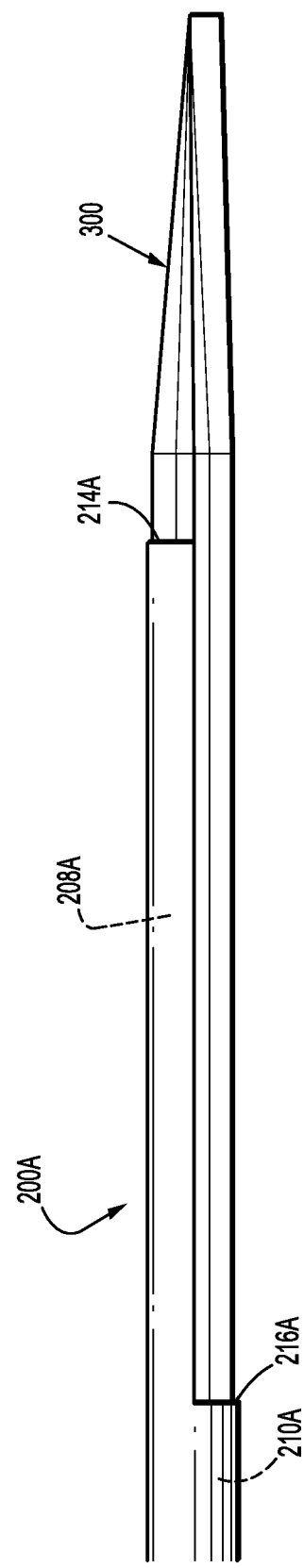
FIG. 3A is a partial, side view of another embodiment of a catheter including a staggered tip design with the presently disclosed insertion stylet inserted therein.
Figure 3B:
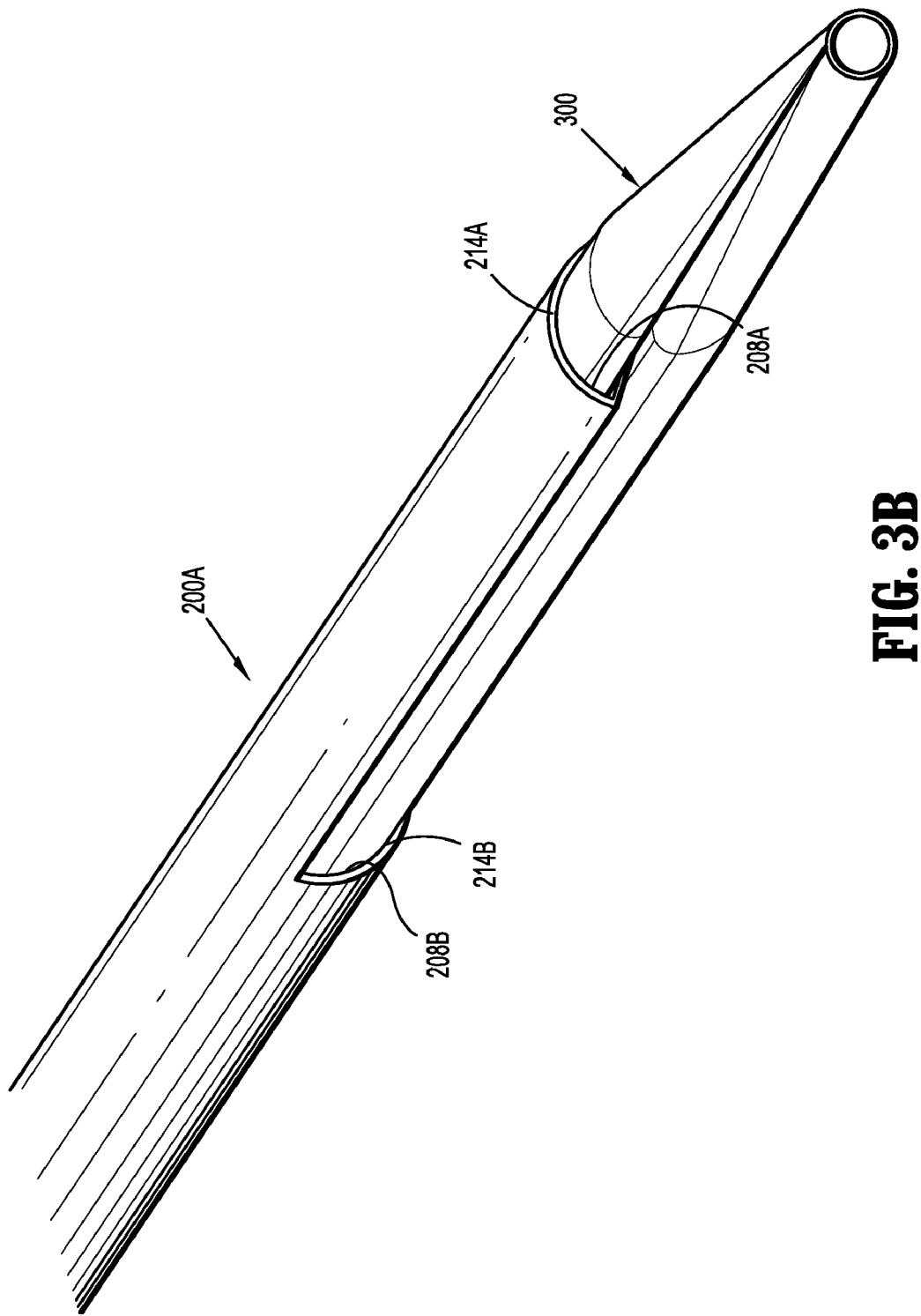
FIG. 3B is an isometric view of the catheter and the insertion stylet seen in FIG. 3A.
Figure 3C:
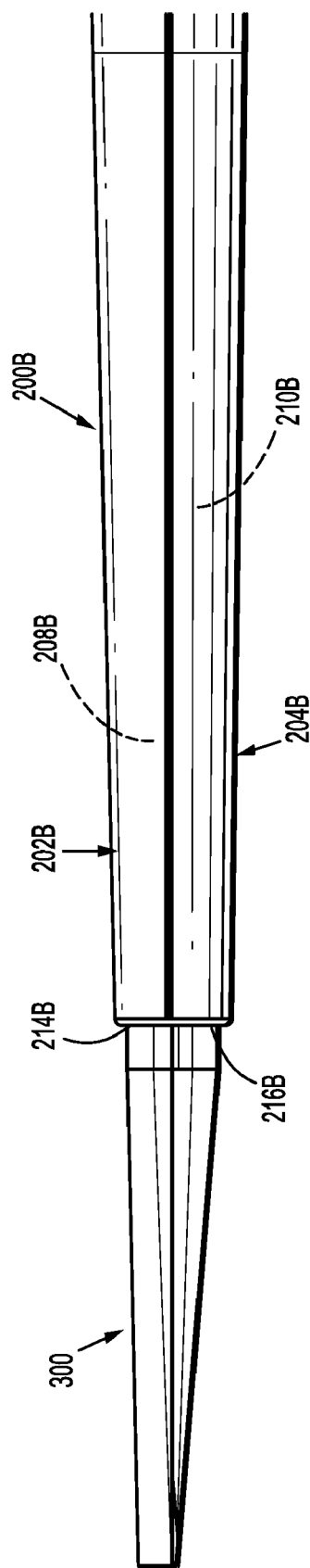
FIG. 3C is a partial, side view of another embodiment of a catheter including a split-tip design with the presently disclosed insertion stylet inserted therein.

As mentioned above, the present disclosure contemplates use of the stylet 300 in connection with both staggered tip catheters, such as the catheter 200A shown in FIGS. 3A and 3B, and split-tip catheters, such as the catheter 200B shown in FIGS. 3C and 3D. As seen in FIGS. 3A and 3B, the catheter 200A includes a staggered tip design, wherein the first and second lumens 208A, 210A extending through the catheter 200A respectively include distal ends 214A, 216A that are offset from each other along the longitudinal axis of the catheter 200A. By contrast, as seen in FIGS. 3C and 3D, the catheter 200B includes a split-tip design incorporating a first tip section 202B with a distal end 214B, through which the first lumen 208B extends, and a second tip section 204B with a distal end 216B, through which the second lumen 210B extends. Although not specifically illustrated in FIGS. 3C and 3D, the respective first and second tip sections 202B, 204B are individual components, which can be spaced apart from each other.

As seen in FIGS. 3A and 3B, upon insertion of the stylet 300 into the catheter 200A, the insertion stylet 300 extends beyond the respective distal ends 214A, 216A of the lumens 208A, 210A. Likewise, as seen in FIGS. 3C and 3D, upon insertion of the stylet 300 into the catheter 200B, the insertion stylet 300 extends beyond the respective distal ends 214B, 216B of the lumens 208B, 210B. In the embodiment of the split-tip catheter 200B illustrated in FIGS. 3C and 3D, it is envisioned that, prior to insertion of the stylet 300, the respective first and second tip sections 202B, 204B may diverge from one another, as is known in the art. The stylet 300 will bring the tip sections 202B, 204B together for insertion after the insertion stylet 300 is inserted into the catheter 200B.

Although the respective distal ends 214B, 216B of the first and second tip sections 202B, 204B are illustrated as being aligned with each other along the longitudinal axis of the catheter 200B in the embodiment shown in FIGS. 3C and 3D, in alternative embodiments, it is envisioned that the respective distal ends 214B, 216B of the first and second tip sections 202B, 204B may be spaced apart from each other along the longitudinal axis of the catheter 200B, similar to the staggered design shown in FIGS. 3A, 3B.

Referring now to FIGS. 2-17, the insertion stylet 300 will be discussed in detail. The insertion stylet 300 is configured and dimensioned to facilitate insertion of the catheter 200 into target tissue, e.g., a body vessel, and has particular application in connection with a hemodialysis procedure. The insertion stylet 300 is formed from a material having a higher durometer than the material comprising the catheter 200, whereby positioning of the insertion stylet 300 within the catheter increases the rigidity of the catheter 200.

The insertion stylet 300 extends along a longitudinal axis "X" (FIG. 2), and includes a first elongated stylet portion 302 having a proximal end region 304 and a distal end region 306, and a second elongated stylet portion 308 having a proximal end region 310 and a distal end region 312.

Figure 4:
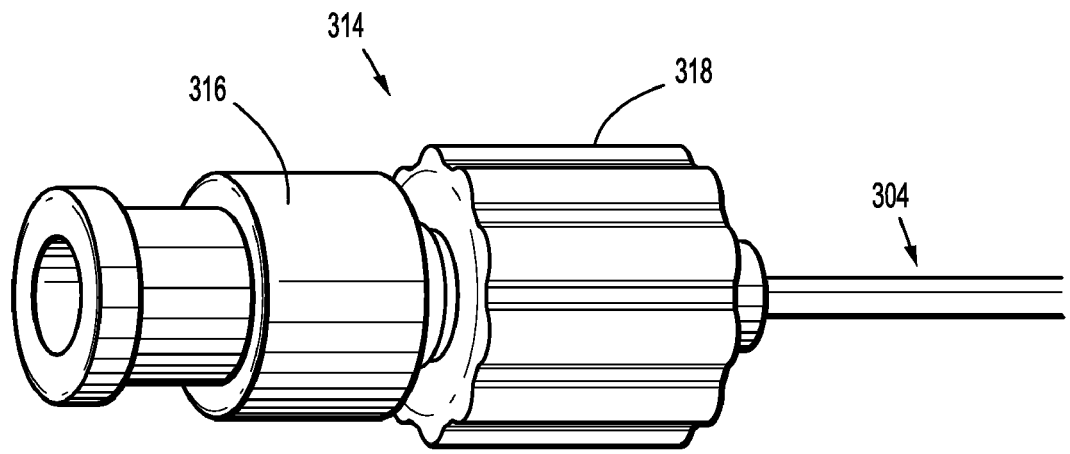
FIG. 4 is a partial side, perspective view of a proximal end of the first stylet portion seen in FIG. 2 including a luer connector and locking structure.
Figure 5:
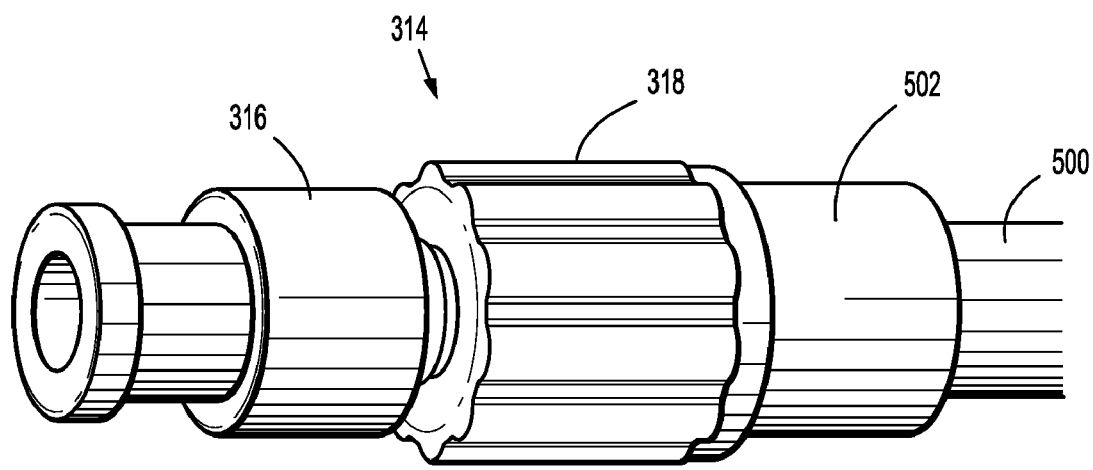
FIG. 5 is a partial side, perspective view of the proximal end of the first stylet portion seen in FIG. 4 positioned within an extension tube.

As seen in FIGS. 4 and 5, in one embodiment of the insertion stylet 300, the proximal end region 304 of the first stylet portion 302 is mechanically connected to, and extends distally from, a first stylet hub 314. The first stylet hub 314 is configured and dimensioned to facilitate manual engagement of the first stylet portion 302 by the clinician, and may be any structure suitable for this intended purpose. In the illustrated embodiment, the first stylet hub 314 includes a luer connector 316 that is adapted for connection to a fluid source, such as a source of saline for irrigation purposes, or to a source of vacuum. To facilitate such connection, it is envisioned that the luer connector 316 may include any suitable structure, such as a partial thread, a bayonet coupling, or the like. The first stylet hub 314 further includes locking structure 318 that is configured and dimensioned for engagement with corresponding locking structure 502 included on an extension tube 500 (FIG. 5) component of an extension tube assembly (not shown) to facilitate a releasable connection therewith. One example of a suitable extension tube assembly is discussed in U.S. Provisional Patent Application Ser. No. 61/141,518, filed on Dec. 30, 2008, the entire contents of which are incorporated by reference herein.

The proximal end region 310 of the second stylet portion 308 may be identical to that of the first stylet portion 302. That is, the proximal end region 310 of the second stylet portion 308 may include a second stylet hub with a luer connector and locking structure that is configured and dimensioned for engagement with corresponding locking structure included on another extension tube. Accordingly, and in the interests of brevity, the proximal end region 310 of the second stylet portion 308 will not be discussed in further detail, and is not illustrated in the figures.

With particular reference to FIGS. 6-17, the respective distal end regions 306, 312 of the first and second stylet portions 302, 308 will be described. The distal end region 306 of the first stylet portion 302 defines an inner face 320 (FIGS. 7, 8) including mating structure 324, and the distal end region 312 of the second stylet portion 308 defines an inner face 322 (FIGS. 10, 11) including mating structure 326. The mating structures 324, 326 correspond in configuration and dimensions, and are adapted for engagement to facilitate the creation of a releasable connection between the first stylet portion 302 and the second stylet portion 308. When the mating structure 324 included at the distal end region 306 of the first stylet portion 302 is in engagement with the mating structure 326 included at the distal end region 312 of the second stylet portion 308, as shown in FIGS. 13-17, the respective distal end portions 306, 312 of the first and second stylet portions 302, 308 cooperatively define a penetrating portion 328 that is configured and dimensioned to facilitate distal advancement of the insertion stylet 300 through tissue.

The mating structures 324, 326 are configured and dimensioned to facilitate relative slidable movement between the first stylet portion 302 and the second stylet portion 308 along the longitudinal axis "X" (FIG. 2) such that the respective first and second stylet portions 302, 308 are independently movable relative to each other, and relative to the catheter 200. This enables sequential removal of the respective first and second stylet portions 302, 308 from the catheter 200. Alternatively, it is envisioned that the respective first and second stylet portions 302, 308 can be manipulated to cause disengagement of the mating structures 324, 326, whereby the respective first and second stylet portions 302, 308 can be subsequently removed from the catheter 200 in unison.

In one embodiment, the mating structure 324 included at the distal end region 306 of the first stylet 302 includes a rib 330 (FIGS. 7, 8), and the mating structure 326 included at the distal end region 312 of the second stylet 308 includes a channel 332 (FIGS. 10, 11) that is configured and dimensioned to receive the rib 330. In the embodiment of the insertion stylet 300 illustrated in FIGS. 6-17, the rib 330 and the channel 332 are configured and dimensioned for engagement in a dovetail arrangement. Specifically, the rib 330 includes tapered sidewalls 334 and the channel 332 includes tapered sidewalls 336. The tapered sidewalls 334, 336 are configured and dimensioned for engagement to inhibit relative movement between the distal end region 306 (FIGS. 7-9) of the first stylet portion 302 and the distal end region 312 (FIGS. 10-12) of the second stylet portion 308 along a transverse axis, i.e., along an axis that intersects the longitudinal axis "X" (FIG. 2) of the stylet 300. It is also envisioned, however, that the tapered configuration of the sidewalls 334, 336 respectively included on the rib 330 and the channel 332 may be omitted, as seen in FIGS. 18-21. In this embodiment, the rib 330 is configured and dimensioned to frictionally engages the channel 332 to thereby resist transverse movement of the distal end region 306 (FIG. 6) of the first stylet portion 302 relative to the distal end region 312 of the second stylet portion 308. However, upon the application of a predetermined force to either or both of the respective first and second stylet portions 302, 308, the configuration of the rib 330 and the channel 332 allows for relative transverse movement between the respective distal end regions 306, 312 (FIG. 6) of the first and second stylet portions 302, 308. Thus, in this embodiment, the respective first and second stylet portions 302, 308 can be removed from the catheter 200 (FIG. 2-2D) either sequentially or in unison.

It is envisioned that at least one of the respective first and second stylet portions 302, 308 (FIG. 2), e.g., the first stylet portion 302, may include a channel 338 (FIGS. 13, 14) extending therethrough that is configured and dimensioned to receive a guidewire (not shown) to facilitate placement of the catheterization system 1000 within the target tissue, as will be described in further detail below. It is also envisioned that the channel 338 may be employed in the infusion of a fluid, such as a medicament or the like into a patient, or that one of lumens 208, 210 (FIG. 3) extending through the catheter 200 (FIG. 2) may serve as a guidewire channel.

With reference again to FIG. 2, the introducer sheath 400 included in the catheterization system 1000 will be discussed. The introducer sheath 400 is similar to the introducer sheath 100 discussed above with respect to FIG. 1, and accordingly, will only be discussed with respect to any differences therefrom.

The introducer sheath 400 is used during placement of the catheter 200, and includes a tubular body portion 402 with a proximal region 404 and a distal region 406. The body portion 402 of the introducer sheath 400 defines an internal lumen 408 (shown in phantom in FIG. 2) that is configured and dimensioned to receive the catheter 200.

The distal region 406 of the introducer sheath 400 includes a portion 410 that tapers distally to approximate an outer dimension of the tapered penetrating portion 328 cooperatively defined by the distal end regions 306, 312 of the first and second stylet portions 302, 308, respectively. The introducer sheath 400 is dimensioned such that the insertion stylet 300 extends beyond the tapered portion 410 thereof when the insertion stylet 300 and the catheter 200 are positioned within the internal lumen 408. As discussed above in connection with the introducer sheath 100 (FIG. 1), the introducer sheath 400 may include one or more perforations 414, e.g., diametrically opposed perforations, and manual grips or members 416 to facilitate tearing of the introducer sheath 400 along the perforation(s) 414.

Referring now to FIGS. 2-17, the use and operation of the stylet member 300 (FIG. 2) to facilitate placement of the catheter 200 will be discussed during the course of a hemodialysis procedure. Initially, a hollow needle cannula (not shown) is inserted into the target body vessel to create a venotomy (entry) site. For example, the needle cannula may be disposed within the skin of the subject, adjacent the neck and clavicle, for accessing a vein. Upon positioning the needle cannula within the target vessel, a guidewire (not shown) is inserted through a proximal end of the needle cannula to a desired location within the body vessel. The needle cannula is then withdrawn, leaving a distal end of the guidewire positioned within the target vessel, and a proximal end of the guidewire extending outwardly from the patient's body. Following placement, the guidewire is introduced to the catheterization system 1000 (FIG. 2).

Figure 6:
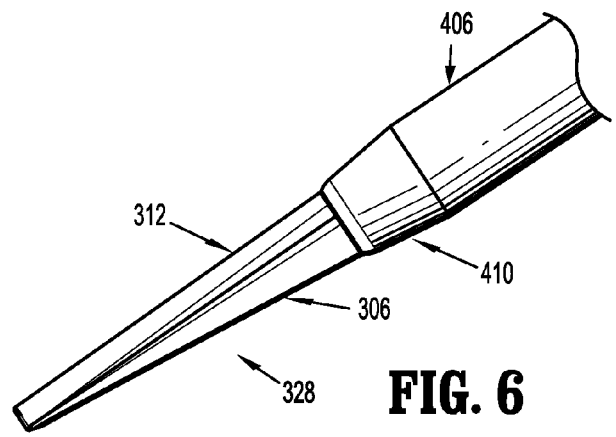
FIG. 6 is a side, perspective view of a distal end portion of the catheterization system shown in FIG. 2 illustrating the first and second stylet portions extending beyond a distal end of the introducer sheath.
Figure 7:
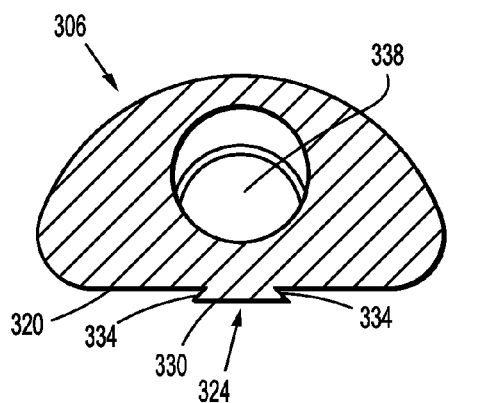
FIG. 7 is a partial, rear, cross-sectional view of the first stylet portion illustrating a distal end region thereof.
Figure 8:
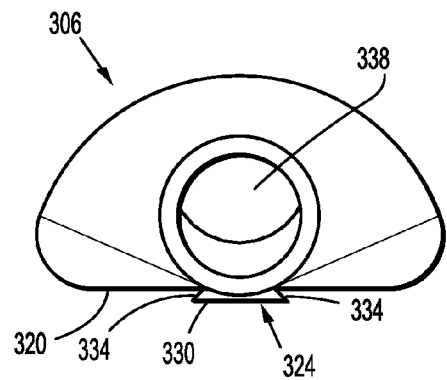
FIG. 8 is a partial front view of the distal end region of the first stylet portion.
Figure 9:
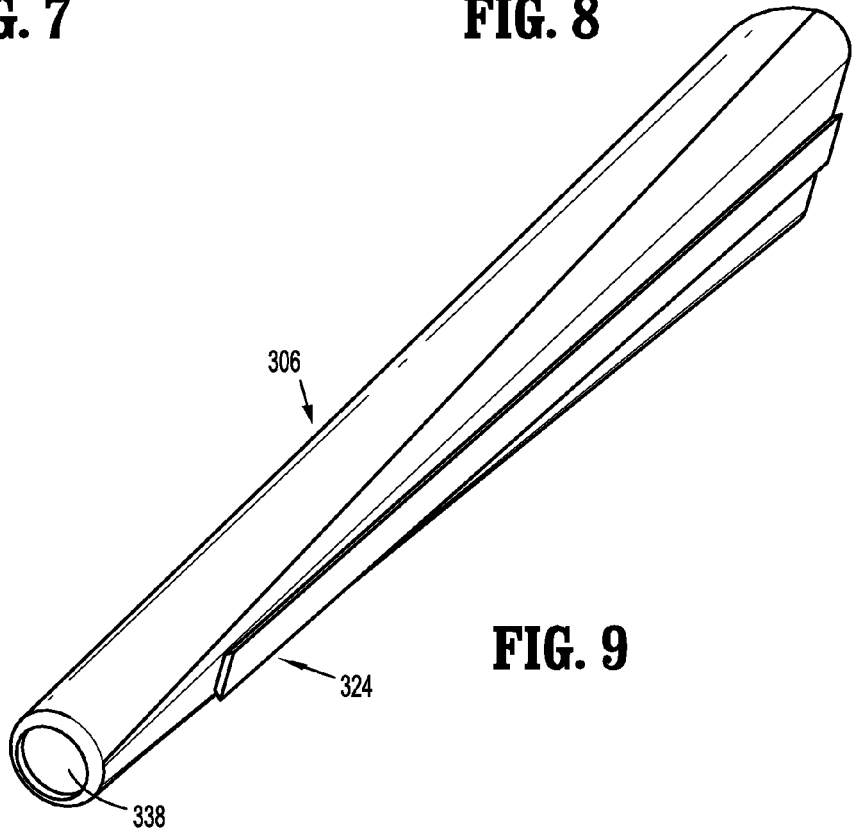
FIG. 9 is a partial side, perspective view of the distal end region of the first stylet portion.
Figure 10:
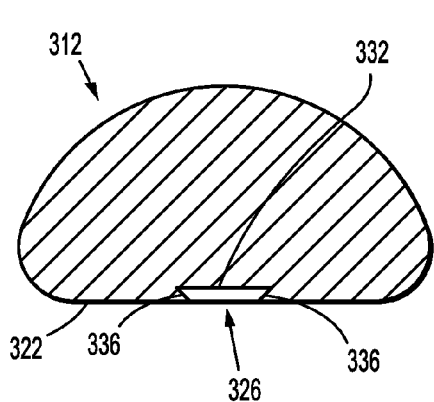
FIG. 10 is a partial, rear, cross-sectional view of the second stylet portion illustrating a distal end region thereof.
Figure 11:
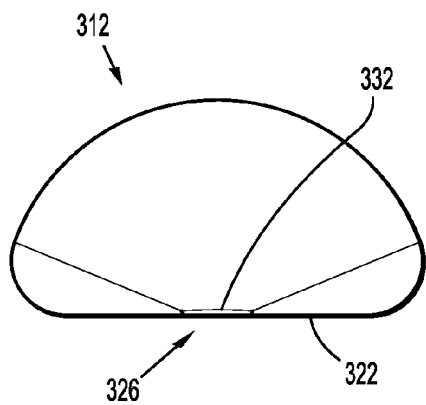
FIG. 11 is a partial front view of the distal end region of the second stylet portion.
Figure 12:
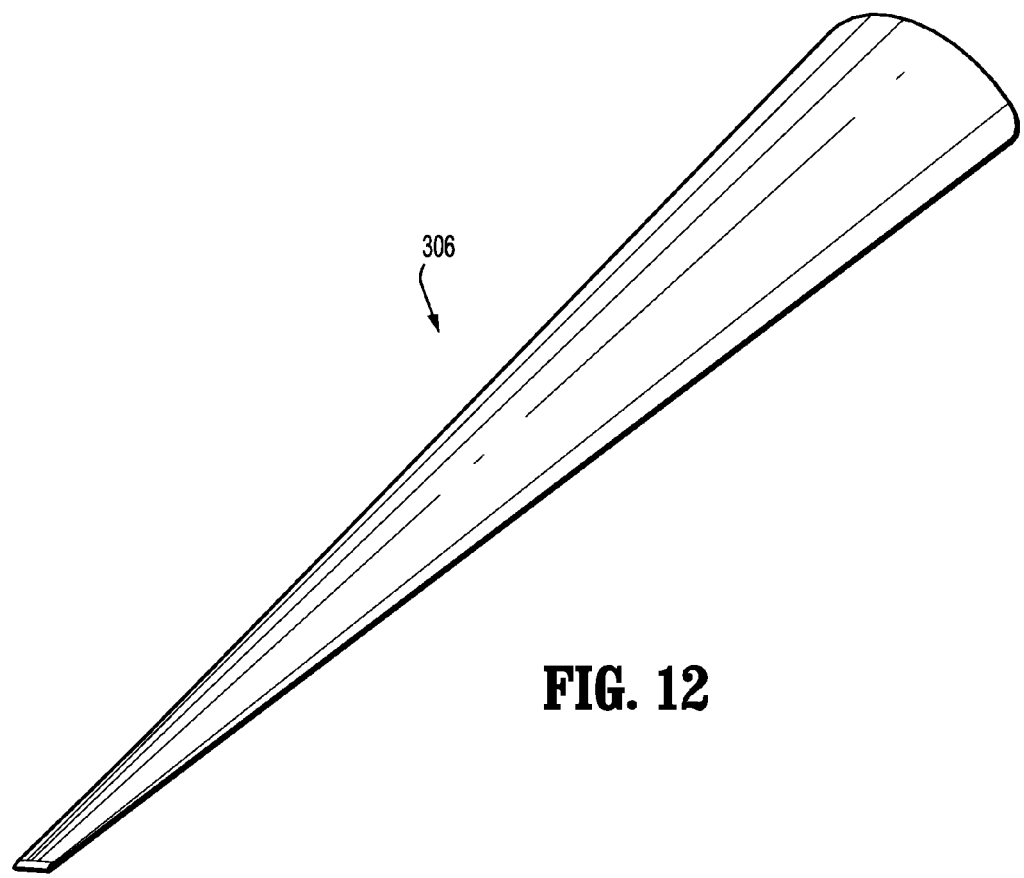
FIG. 12 is a partial side, perspective view of the distal end region of the second stylet portion.
Figure 14:
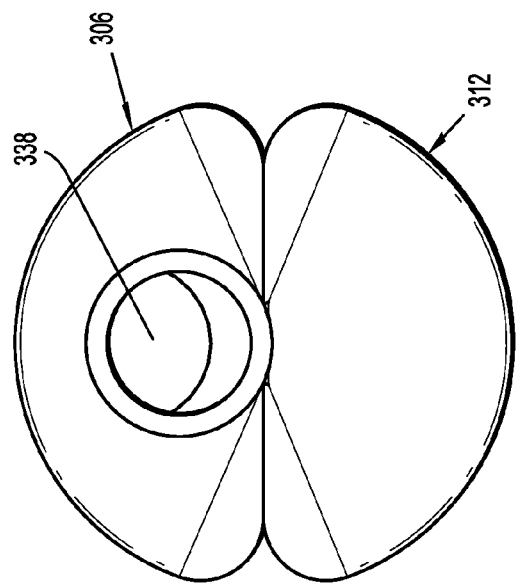
FIG. 14 is a partial front view of the distal end regions of the first and second stylet portions upon engagement.
Figure 15:
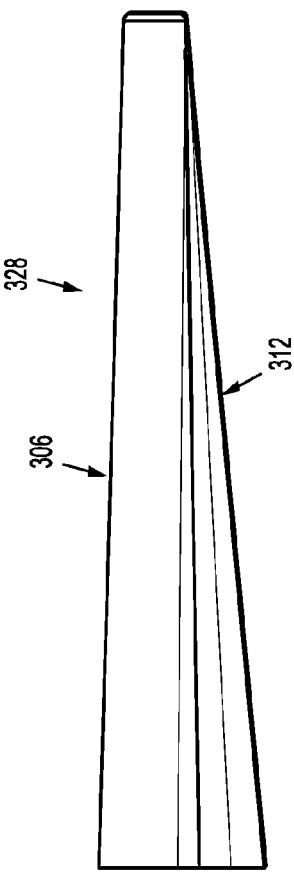
FIG. 15 is a partial side view of the distal end regions of the first and second stylet portions shown in FIG. 14 upon engagement.
Figure 13:
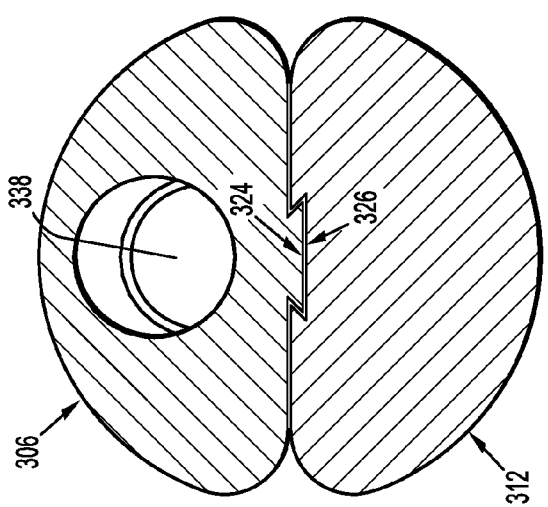
FIG. 13 is a partial, rear, cross-sectional view of the first and second stylet portions illustrating the distal end regions thereof upon engagement.
Figure 19:
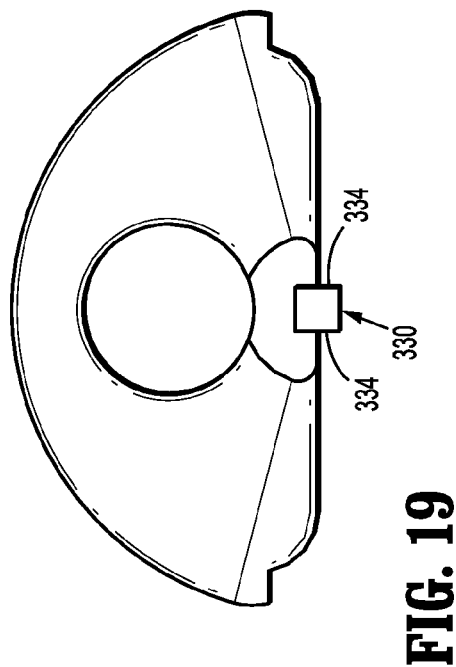
FIG. 19 is a partial front view of the distal end region of the first stylet portion shown in FIG. 18.
Figure 21:
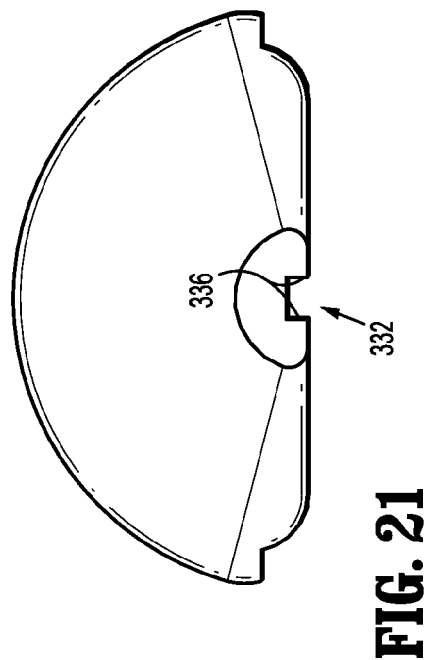
FIG. 21 is a partial front view of the distal end region of the second stylet portion shown in FIG. 20.
Figure 18:
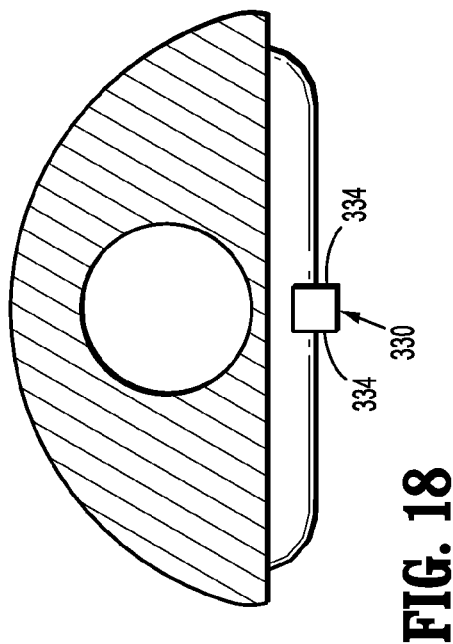
FIG. 18 is a partial, rear, cross-sectional view of the first stylet portion according to an alternative embodiment of the present disclosure illustrating a distal end region thereof.
Figure 20:
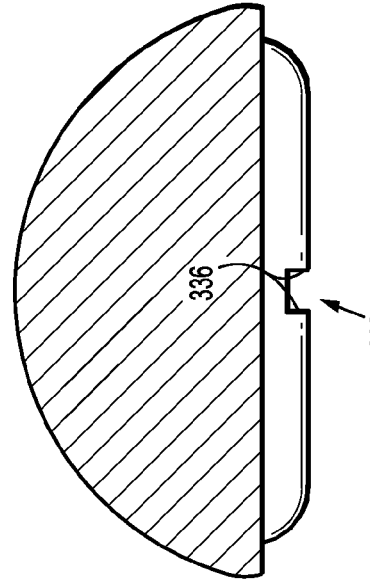
FIG. 20 is a partial, rear, cross-sectional view of the second stylet portion according to an alternative embodiment of the present disclosure illustrating a distal end region thereof.

Either subsequent or prior to placement of the guidewire, the catheter 200 is inserted into, and advanced distally through, the internal lumen 408 (FIG. 2) of the introducer sheath 400. Thereafter, the respective first and second stylet portions 302, 308 are inserted into corresponding extension tubes 500 (FIG. 5), and are advanced distally therethrough into corresponding internal lumens 208, 210 (FIGS. 2A, 3) of the catheter 200. Specifically, the first stylet portion 302 is positioned within the internal lumen 208, and the second stylet portion 308 is positioned within the second lumen 210 (FIG. 2A). The first stylet portion 302 is advanced distally through the internal lumen 208 of the catheter 200 until the distal end region 306 thereof is positioned distally of the distal region 406 of the introducer sheath 400 (FIGS. 2, 6). Likewise, the second stylet portion 308 is advanced distally through the internal lumen 210 of the catheter 200 until the distal end region 312 thereof is positioned distally of the distal region 406 of the introducer sheath 400 (FIGS. 2, 6). The respective distal end regions 306, 312 of the first stylet portion 302 and the second stylet portion 308 are configured and dimensioned such that when the first and second stylet portions 302, 308 are properly positioned within the catheter 200, the respective distal end regions 306, 312 thereof are coterminous (FIGS. 2, 6).

During assembly, the respective first and second stylet portions 302, 308 (FIG. 2) are manipulated such that the mating structure 324 (FIGS. 7-9) included at the distal end region 306 of the first stylet portion 302 engages the mating structure 326 (FIGS. 10-12) included at the distal end region 312 of the second stylet portion 308 to thereby collectively define the penetrating portion 328 (FIGS. 6, 15-17). Thereafter, the locking structures 318 (FIGS. 4, 5) included on the stylet hubs 314 are connected to the corresponding locking structures 502 (FIG. 5) included on the extension tubes 500 to fix the position of the respective first and second stylet portions 302, 308 relative to the extension tubes 500 and the catheter 200.

After positioning of the stylet 300 within the catheter 200 as desired, the proximal end of the guidewire is inserted into the channel 338 (FIGS. 13, 14), which, to reiterate, may be included in either the first stylet portion 302 or the second stylet portion 308. The catheterization assembly 1000 is then advanced distally over the guidewire until at least a portion of the distal region 406 (FIG. 2) of the introducer sheath 400 and at least a portion of the distal end 206 (FIGS. 2B-2D) of the catheter 200 are positioned within the target vessel.

The guidewire and the respective first and second stylet portions 302, 308 (FIG. 2) can then be removed from the catheter 200. The unique mating structures 324, 326 (FIGS. 7-12) respectively included at the distal end regions 306, 312 of the first and second stylet portions 302, 308 allow the first and second stylet portions 302, 308 to be slidably removed from the internal lumens 208, 210 (FIGS. 2A, 3) of the catheter 200 independently of each other, e.g., in either sequential or contemporaneous fashion, as discussed above. In other words, removing the respective first and second stylet portions 302, 308 at the same time is optional, rather than necessary.

At the clinician's election, either prior or subsequent to removal of the guidewire and the respective first and second stylet portions 302, 308, the introducer sheath 400 can be separated from the catheter 200. To facilitate this separation, the clinician grasps and manipulates the manual members 416 to facilitate tearing along the perforation(s) 414 (FIG. 2).

Referring now to FIGS. 22-30, an alternative embodiment of the insertion stylet, referred to generally by the reference character 600, will be discussed. The insertion stylet 600 is similar to the insertion stylet 300 discussed above with respect to FIGS. 2-17, and accordingly, will only be discussed with respect to any differences therefrom.

Figure 23:
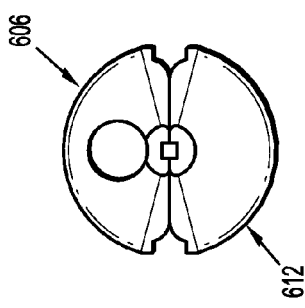
FIG. 23 is a partial front view of the distal end regions of the first and second stylet portions shown in FIG. 22 upon engagement.
Figure 22:
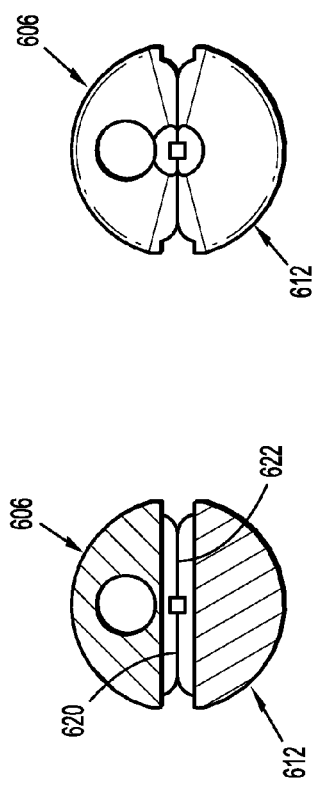
FIG. 22 is a partial, rear, cross-sectional view of the first and second stylet portions shown in FIGS. 18-21 illustrating the distal end regions thereof upon engagement.
Figure 24:
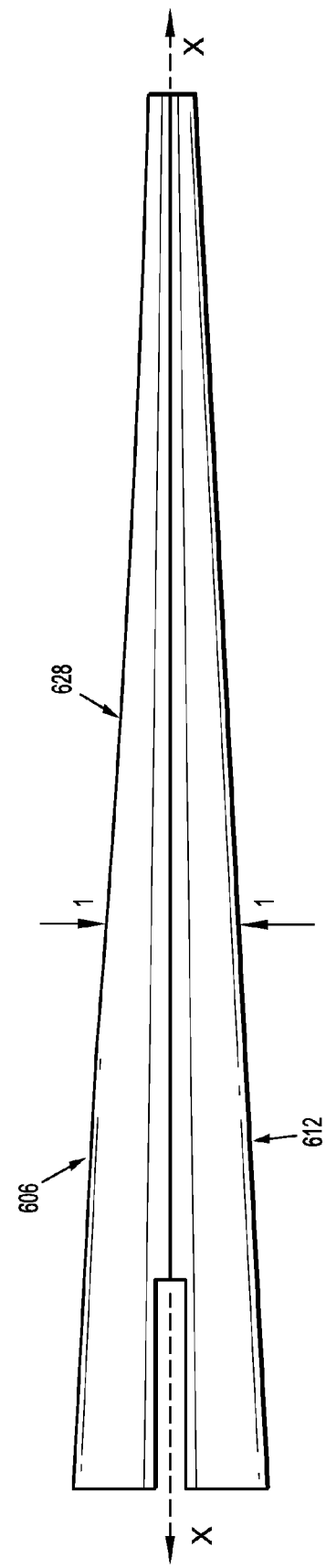
FIG. 24 is a partial side view of the distal end regions of the first and second stylet portions shown in FIG. 22 upon engagement.
Figure 26:
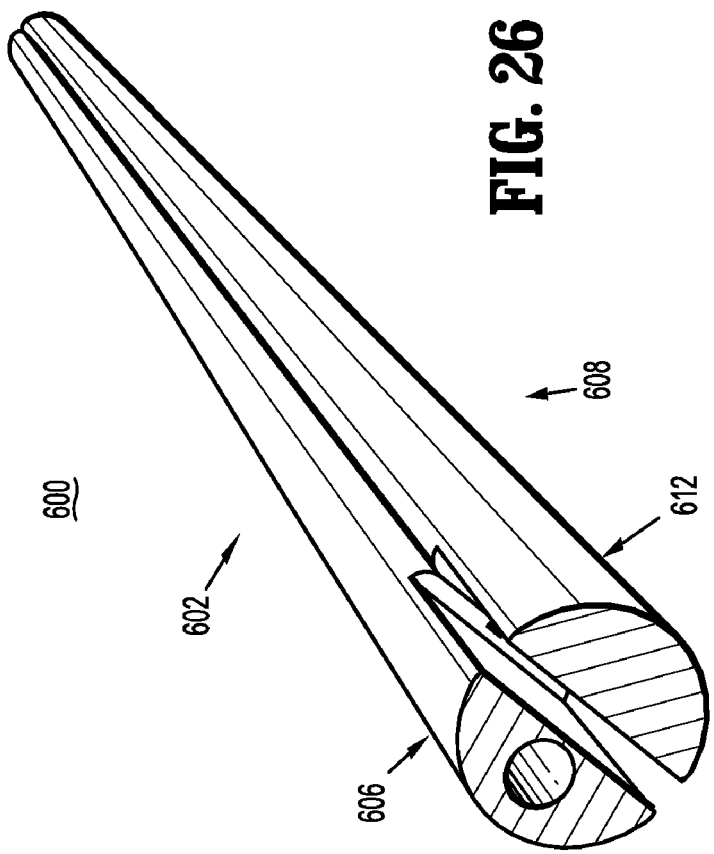
FIG. 26 is a partial rear, cross-sectional view of the distal end regions of the first and second stylet portions shown in FIG. 22 upon engagement shown in perspective.
Figure 25:
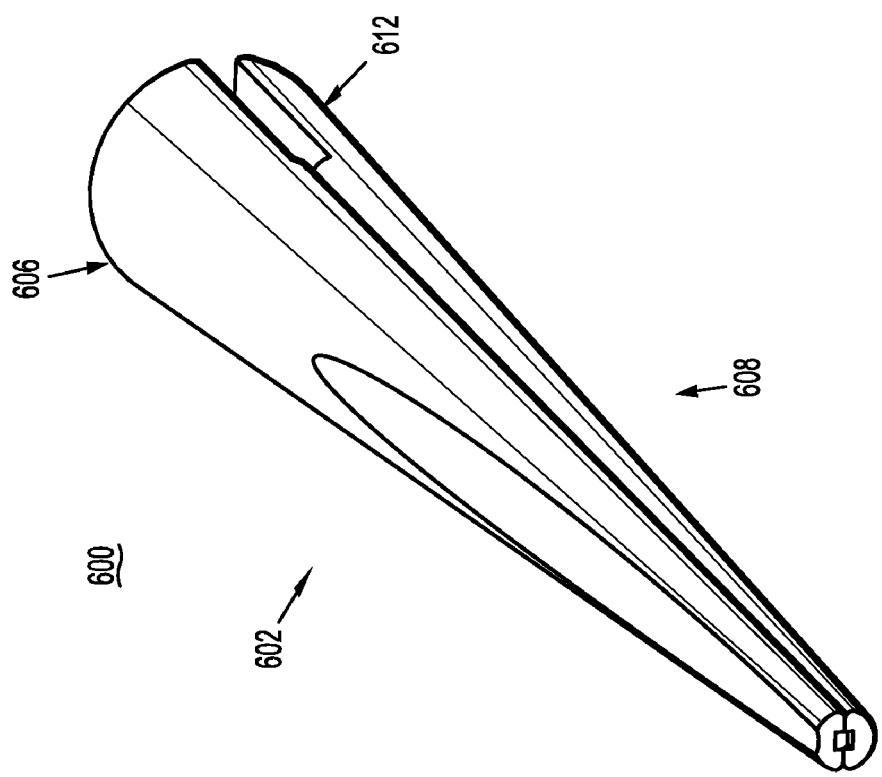
FIG. 25 is a partial front, perspective view of the distal end regions of the first and second stylet portions shown in FIG. 22 upon engagement.
Figure 32:
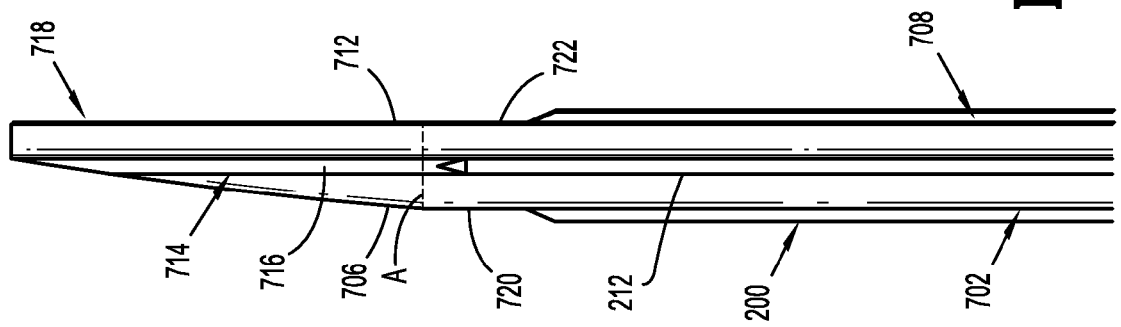
FIG. 32 is partial, longitudinal, cross-sectional view of the insertion stylet and catheter shown in FIG. 31.
Figure 31:
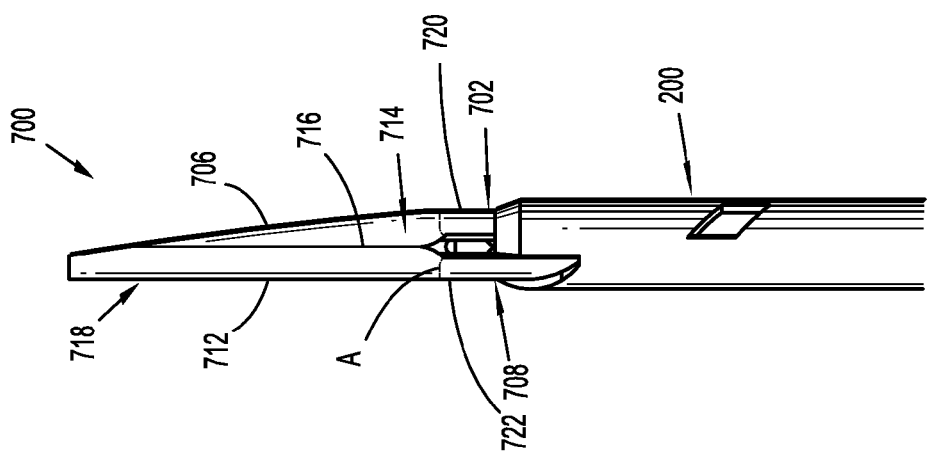
FIG. 31 is partial, side view illustrating an alternate embodiment of the presently disclosed insertion stylet positioned within a catheter, and including first and second stylet portions having conjoined distal end regions.
Figure 33D:
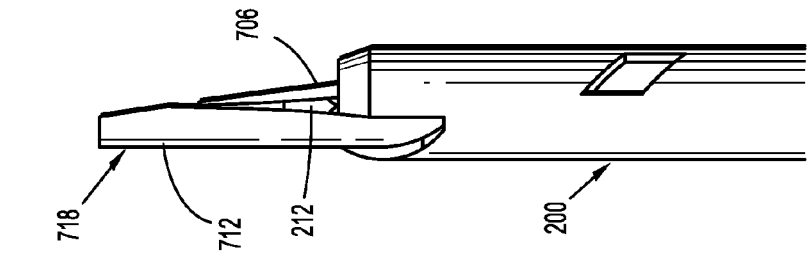
FIGS. 33A-33D are partial, side views illustrating progressive separation of the distal end regions of the first and second stylet portions during withdrawal of the insertion stylet from the catheter.
Figure 33C:
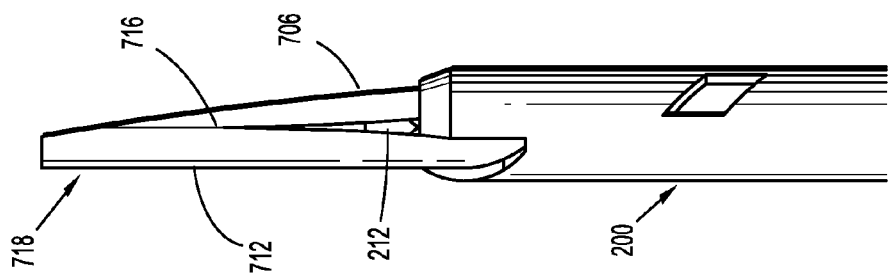
Figure 33B:
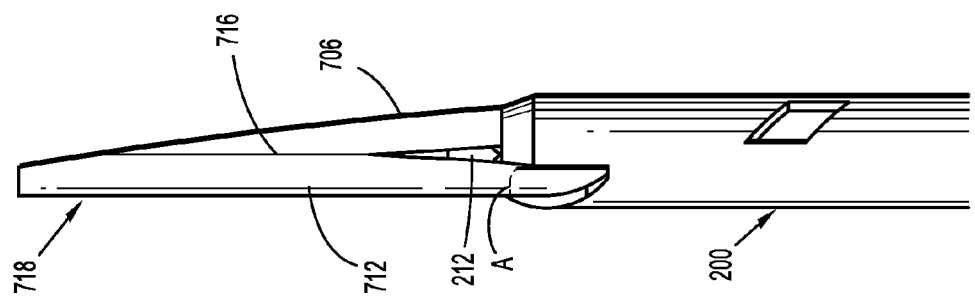
Figure 33A:
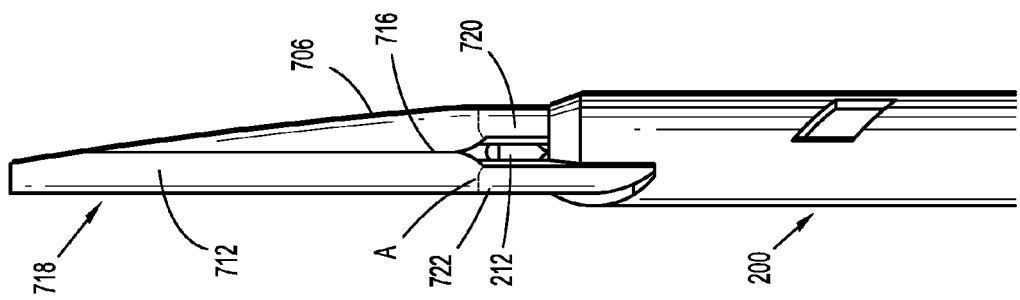

The insertion stylet 600 is configured and dimensioned to facilitate insertion of the catheter 200 (FIGS. 28-30) into target tissue, e.g., a body vessel, and includes first and second stylet portions 602, 608 (FIGS. 25, 26), respectively. As best seen in FIGS. 22 and 23, the respective distal end regions 606, 612 of the first and second stylet portions 602, 608 are devoid of the mating structure 324, 326 (FIGS. 7-12) discussed above in connection with the insertion stylet 300 (FIG. 2). Accordingly, in this embodiment, contact between the inner faces 620, 622 (FIGS. 22, 23) respectively defined by the distal end regions 606, 612 of the first and second stylet portions 602, 608 (FIG. 25) is maintained by the introducer sheath 400 (FIG. 2). In other words, when the respective first and second stylet portions 602, 608 are positioned within the catheter 200 (FIGS. 28-30) such that the respective first and second stylet portions 602, 608 extend beyond the distal region 406 of the introducer sheath 400 (FIG. 2), the introducer sheath 400 acts to apply a force to the respective distal end regions end 606, 612 of the first and second stylet portions 602, 608 that is directed inwardly towards the longitudinal axis "X" (FIG. 24), i.e., e.g., in the direction of arrows 1. This force causes and maintains engagement of the distal end region 606 the first stylet portion 602 with the distal end region 612 of the second stylet portion 608 to thereby define the penetrating portion 628, thus obviating the need for the mating structures 324, 326 (FIGS. 7-12) discussed above.

The configuration of the respective distal end regions 606, 612 of the first and second stylet portions 602, 608 facilitates relative slidable movement between the first stylet portion 602 and the second first stylet portion 608 along the longitudinal axis "X" (FIG. 24) such that the respective first and second stylet portions 602, 608 are independently movable relative to both each other, and the catheter 200. Thus, the respective first and second stylet portions 602, 608 are also removable from the catheter 200 either sequentially or contemporaneously.

With reference now to FIGS. 31-33D, another embodiment of the insertion stylet, referred to generally by the reference character 700, will be discussed. The insertion stylet 700 is similar to the aforedescribed insertion stylet 300 (FIGS. 2-17), and accordingly, will only be discussed with respect to any differences therefrom.

The insertion stylet 700 includes first and second stylet portions 702, 708 with proximal end regions (not shown), and distal end regions 706, 712. Whereas the proximal end regions of the stylet portions 702, 708 are disconnected, and separated from one another (see FIG. 2), the distal end regions 706, 712 are attached by conjoining structure 714. The attachment between the distal end regions 706, 712 established by the conjoining structure 714 substantially inhibits relative longitudinal movement between the stylet portions 702, 708 until such time that relative longitudinal movement between the stylet portions 702, 708 is desirable, e.g., during removal of the insertion stylet 700 from the catheter 200. At that time, a predetermined force is applied to the conjoining structure 714 to separate the distal end regions 706, 712, as will be described below.

The conjoining structure 714 may be any structure suitable for the intended purpose of joining together the respective distal end regions 706, 712 of the stylet portions 702, 708. In the embodiment of the insertion stylet 700 illustrated in FIGS. 31-33D, for instance, the conjoining structure 714 is illustrated as a thin wall 716 positioned between the distal end regions 706, 712. The thin wall 716 maintains the attachment between the distal end regions 706, 712 during insertion of the stylet 700, but allows for selective detachment of the distal end regions 706, 712 thereafter such that the stylet 700 can be separated into two distinct components that can be removed from the catheter 200 in the manner set forth above.

To separate the distal end regions 706, 712, it is envisioned that the thin wall 716 may be caused to engage the septum wall 212 separating the lumens 208, 210 (FIG. 3) of the catheter 200. Specifically, upon the application of a proximally directed force to either, or both, of the stylet portions 702, 708, the septum wall 212 is brought into engagement with the thin wall 716, thereby shearing, or tearing, the thin wall 716, and separating the stylet portion 702 from the stylet portion 708, as shown in the transition illustrated in FIGS. 33A-33D. To further facilitate separation of the stylet portions 702, 708, it is contemplated that the thin wall 716 may include a weakened portion (not shown), such as a seam or perforated section.

Following separation of the stylet portions 702, 708, the material comprising the thin wall 716 remains attached to either, or both, of the distal end regions 706, 712 such that the material comprising the thin wall 716 is withdrawn from the catheter 200 through the lumens 208, 210 contemporaneously with the stylet portions 702, 708.

In the embodiment of the disclosure illustrated in FIGS. 31-33D, the distal end regions 706, 712 are configured to define a conical tip 718 that includes the thin wall 716. The conical tip 718 is secured to both a distal end 720 of the first stylet portion 702, and a distal end 722 of the second stylet portion 708.

Various methods of forming the conical tip 718, and attaching the conical tip 718 to the stylet portions 702, 708, are contemplated herein. For example, it is contemplated that the conical tip 718 may be individually formed, and thereafter, secured to the distal ends 720, 722 of the stylet portions 702, 708, as indicated by the phantom line "A" in FIGS. 31-33B. In such embodiments, it is envisioned that the conical tip 718 may formed, and thereafter, insert-molded onto the distal ends 720, 722 of the stylet portions 702, 708 following positioning of the stylet portions 702, 708 within the lumens 208, 210 (FIG. 3) of the catheter 200. Alternatively, the conical tip 718 may be injection molded, and then welded, e.g., RF or ultrasonically welded, onto the respective distal ends 720, 722 of the stylet portions 702, 708.

It is also contemplated herein that the conical tip 718 may be monolithically formed with the distal ends 720, 722 of the stylet portions 702, 708. In such embodiments, following positioning of the stylet portions 702, 708 within the lumens 208, 210 (FIG. 3) of the catheter 200, the respective distal ends 720, 722 of the stylet portions 702, 708 may be reconfigured into the conical tip 718. For example, the respective distal ends 720, 722 of the stylet portions 702, 708 may be pressed together, and heated, e.g., via the use of an RF welder and a die, whereby the thin wall 716 of the conical tip 718 is joined together to monolithically form the conical tip 718 with the stylet portions 702, 708.

Figure 34:
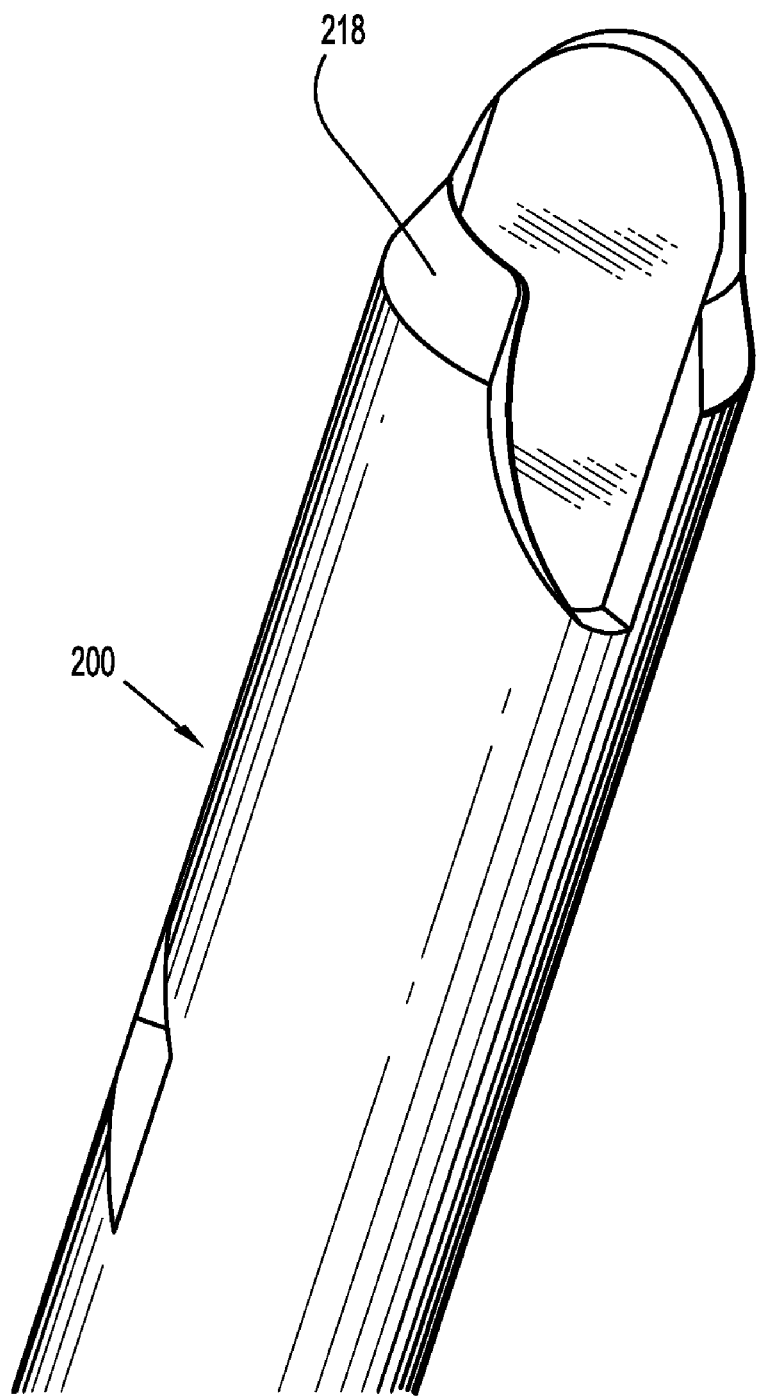
FIG. 34 is a partial, side, perspective view of one embodiment of a catheter for use with the insertion stylet seen in FIGS. 31-33D.

When the insertion stylet 700 is utilized in connection with chronic dialysis catheters, such as the catheter 200 seen in FIG. 34, it is envisioned that edges 218 along an outer portion of the catheter 200 surrounding the distal tip may be chamfered, as illustrated in FIG. 34. Including chamfered edges 218 allows for a smooth transition between the insertion stylet 700 and the catheter 200.

The insertion stylet 700 provides advantages to both the user and the manufacturer over those insertion methods known in the art, such as using a sheath. For example, insertion stylet 700 minimizes the number of steps and components in the insertion process, thereby reducing the overall time necessary for, and increasing the ease of, insertion, which in turn may reduce the time necessary to perform, and consequently, the costs associated with, the surgical procedure. Additionally, vis-á-vis insertions using a sheath, the insertion stylet 700 is easier and less costly to manufacture, which allows for reductions in the costs and resources associated with manufacturing.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the invention based on the above-described embodiments. Accordingly, the invention is not to be limited by what has been particularly shown and described, except as indicated by the appended claims.

What is claimed is:

1. A stylet, comprising:
a first stylet portion having proximal and distal end regions, the first stylet portion being configured and dimensioned to be slidably positioned within a first lumen of a catheter; and
a second stylet portion having proximal and distal end regions, the second stylet portion being configured and dimensioned to be slidably positioned within a second lumen of the catheter which is separated from the first lumen by a septum wall, wherein the first and second stylet portions extend from a proximal end of the catheter to beyond a distal end of the catheter, the first and second stylet portions including corresponding mating structure fixedly secured thereto for releasably joining the distal end regions of the first and second stylet portions, the first and second stylet portions being independently movable in relation to each other to facilitate selective removal of the first stylet portion and/or the second stylet portion from the catheter, the distal end regions of the first and second stylet portions together defining a tapered penetrating portion.

2. The stylet of claim 1, wherein the distal end regions of the first and second stylet portions are substantially coterminous.

3. The stylet of claim 1, wherein the stylet is formed from a material that is more rigid than the catheter such that positioning of the stylet within the catheter increases rigidity of the catheter.

4. The stylet of claim 1, wherein the corresponding mating structure is positioned at the distal end regions of the first and second stylet portions.

5. The stylet of claim 1, wherein the corresponding mating structure included on the first and second stylet portions is configured to facilitate relative slidable movement between the first and second stylet portions.

6. The stylet of claim 1, wherein the corresponding mating structure includes a frangible weld common to the distal end regions of the first and second stylet portions, the weld being configured and dimensioned for engagement with the septum wall upon withdrawal of the first and second stylet portions from the catheter, whereby the distal end region of the first stylet portion is separated from the distal end region of the second stylet portion.

7. The stylet of claim 1, wherein the mating structure included on the first stylet portion includes a rib and the mating structure included on the second stylet portion includes a channel configured and dimensioned to slidably receive the rib.

8. The stylet of claim 7, wherein the rib and the channel are configured and dimensioned to allow relative transverse movement between the first and second stylet portions.

9. The stylet of claim 7, wherein the rib and the channel are configured and dimensioned to prevent relative transverse movement between the first and second stylet portions.

10. The stylet of claim 9, wherein the rib and the channel each include a dovetail configuration.

11. The stylet of claim 1, wherein the first stylet portion defines a channel configured and dimensioned to receive a guidewire.

12. The stylet of claim 1, wherein the first stylet portion corresponds in configuration to the first lumen of the catheter and the second stylet portion corresponds in configuration to the second lumen of the catheter.

13. A catheterization system, comprising:
a catheter including a body having proximal and distal ends and defining first and second lumens extending therethrough, wherein the first and second lumens are separated by a septum wall; and
a stylet including a first stylet portion having proximal and distal end regions, and a second stylet portion having proximal and distal end regions, the first stylet portion being configured and dimensioned to be slidably positioned within the first lumen of the catheter and the second stylet portion being configured and dimensioned to be slidably positioned within the second lumen of the catheter, wherein the first and second stylet portions extend from the proximal end of the catheter to beyond the distal end of the catheter, the first and second stylet portions including corresponding mating structure fixedly secured thereto for releasably joining the distal end regions of the first and second stylet portions, the first and second stylet portions being independently movable in relation to each other to facilitate selective removal of the first stylet portion and/or the second stylet portion from the catheter, the distal end regions of the first and second stylet portions together defining a tapered penetrating portion.

14. The catheterization system of claim 13 further comprising a sheath having proximal and distal ends and defining a sheath lumen configured and dimensioned to receive the catheter, wherein the stylet is dimensioned to extend beyond the distal end of the sheath when the stylet is positioned within the catheter such that the sheath forces the distal end regions of the first and second stylet portions into engagement with each other to define the penetrating portion of the stylet.

15. The catheterization system of claim 14, wherein the sheath further includes a perforated section to facilitate tearing of the sheath.

16. A method of positioning a catheter within a tissue site comprising the steps of:
positioning a first stylet portion of a stylet within a first lumen of the catheter and positioning a second stylet portion of the stylet within a second lumen of the catheter, the first and second stylet portions extending from a proximal end of the catheter and beyond a distal end of the catheter, wherein at least the first stylet portion defines a channel therethrough configured to receive a guidewire;
attaching corresponding mating structure provided at distal end regions of the first and second stylet portions to thereby connect a distal end region of the first stylet portion to a distal end region of the second stylet portion such that the first and second stylet portions are independently movable;
advancing the stylet and the catheter distally over a guidewire positioned within the tissue site until a distal end of the catheter is positioned within the tissue site; and
withdrawing the stylet from the catheter by detaching the corresponding mating structure at the distal end regions of the first and second stylet portions.

17. A catheterization system, comprising:
a catheter including a body having proximal and distal ends and defining first and second lumens extending therethrough, wherein the first and second lumens are separated by a septum wall; and
a stylet including a first stylet portion with proximal and distal end regions configured and dimensioned for insertion into the first lumen of the catheter, and a second stylet portion with proximal and distal end regions configured and dimensioned for insertion into the second lumen of the catheter, wherein the proximal end regions of the first and second stylet portions are separated from one another, and the distal end regions of the first and second stylet portions are connected by conjoining structure to thereby inhibit relative longitudinal movement between the distal end regions of the first and second stylet portions until a predetermined force is applied to the stylet, wherein the conjoining structure is a weld.

18. A catheterization system, comprising:
a catheter including a body having proximal and distal ends and defining first and second lumens extending therethrough, wherein the first and second lumens are separated by a septum wall: and
a stylet including a first stylet portion with proximal and distal end regions configured and dimensioned for insertion into the first lumen of the catheter, and a second stylet portion with proximal and distal end regions configured and dimensioned for insertion into the second lumen of the catheter, wherein the proximal end regions of the first and second stylet portions are separated from one another, and the distal end regions of the first and second stylet portions are connected by conjoining structure to thereby inhibit relative longitudinal movement between the distal end regions of the first and second stylet portions until a predetermined force is applied to the stylet, wherein the conjoining structure is configured and dimensioned such that the predetermined force is applied to the conjoining structure by the septum wall of the catheter upon withdrawal of at least one of the first and second stylet portions from the catheter, whereby the first stylet portion is separated from the second stylet portion to permit relative longitudinal movement therebetween.

19. The stylet of claim 1, wherein the penetrating portion includes an external wall surface defining a transverse cross-sectional dimension decreasing in a distal direction.

20. The catheterization system of claim 13, wherein the penetrating portion includes an external wall surface defining a transverse cross-sectional dimension decreasing in a distal direction.

21. A catheterization system, comprising:
a catheter including a body having proximal and distal ends and defining first and second lumens extending therethrough, wherein the first and second lumens are separated by a septum wall; and
a stylet including a first stylet portion with proximal and distal end regions configured and dimensioned for insertion into the first lumen of the catheter, and a second stylet portion with proximal and distal end regions configured and dimensioned for insertion into the second lumen of the catheter, wherein the proximal end regions of the first and second stylet portions are separated from one another, and the distal end regions of the first and second stylet portions are connected by conjoining structure to thereby inhibit relative longitudinal movement between the distal end regions of the first and second stylet portions until a predetermined force is applied to the stylet, the conjoining structure being configured and dimensioned such that the predetermined force acts on the conjoining structure to separate the distal end regions of the first and second stylet portions without damaging the first and second stylet portions thereby enabling relative longitudinal movement between the distal end regions of the first and second stylet portions.

* * * * *